(12) United States Patent
Kamiya et al.

(10) Patent No.: US 10,365,243 B2
(45) Date of Patent: Jul. 30, 2019

(54) GAS SENSOR PROVIDED WITH FLANGE PORTION OF COVER THEREOF

(71) Applicant: DENSO CORPORATION, Kariya, Aichi-pref. (JP)

(72) Inventors: Yasutaka Kamiya, Kariya (JP); Yoshihide Segawa, Kariya (JP); Hirokazu Yamada, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/886,052

(22) Filed: Feb. 1, 2018

(65) Prior Publication Data

US 2018/0217089 A1    Aug. 2, 2018

(30) Foreign Application Priority Data

Feb. 2, 2017    (JP) ................. 2017-017789

(51) Int. Cl.
| | |
|---|---|
| *G01N 27/407* | (2006.01) |
| *G01N 27/403* | (2006.01) |
| *F01N 13/00* | (2010.01) |
| *G01M 15/10* | (2006.01) |
| *G01N 27/406* | (2006.01) |
| *G01N 27/41* | (2006.01) |

(Continued)

(52) U.S. Cl.
CPC ....... *G01N 27/4078* (2013.01); *F01N 13/008* (2013.01); *G01M 15/104* (2013.01); *G01N 27/409* (2013.01); *G01N 27/4067* (2013.01); *G01N 27/4071* (2013.01); *G01N 27/41* (2013.01); *G01N 33/0037* (2013.01); *F01N 2560/025* (2013.01); *Y02A 50/245* (2018.01)

(58) Field of Classification Search
CPC .. G01N 27/406; G01N 27/407; G01N 27/416; G01N 27/409; G01N 27/4077; G01N 27/4078
See application file for complete search history.

(56) References Cited

U.S. PATENT DOCUMENTS 4,019,974 A *   4/1977   Weyl .................. G01N 27/4062
                                                    204/428
4,383,907 A     5/1983   Legrand et al.
(Continued)

FOREIGN PATENT DOCUMENTS

| JP | 11-190715 | 7/1999 |
| JP | 2012-083327 | 4/2012 |

(Continued)

*Primary Examiner* — Susan D Leong
(74) *Attorney, Agent, or Firm* — Nixon & Vanderhye P.C.

(57) ABSTRACT

A gas sensor is provided with a sensor element having a detecting portion; an insulator supporting the sensor element in a state where the detecting portion is protruded therefrom, the sensor element being inserted through the insulator; a housing supporting the insulator; an inner cover covering the detecting portion; and an outer cover covering the inner cover.

An inner flange portion of the inner cover and an outer flange portion of the outer cover are supported between the insulator and the housing. A protrusion is formed on a corner portion facing the insulator, the protrusion contacting with the insulator. An end face of the outer flange portion is positioned radially closer to an outer side with respect to a radial direction, than a position of an end face of the inner flange portion.

6 Claims, 14 Drawing Sheets

(51) Int. Cl.
*G01N 33/00* (2006.01)
*G01N 27/409* (2006.01)

(56) References Cited

U.S. PATENT DOCUMENTS

| | | | |
|---|---|---|---|
| 6,214,186 B1 | 4/2001 | Watanabe et al. | |
| 2002/0144538 A1* | 10/2002 | Yamada | G01N 27/4062 73/31.05 |
| 2006/0065541 A1* | 3/2006 | Nishio | G01N 27/4077 205/427 |
| 2012/0031171 A1 | 2/2012 | Masuda et al. | |
| 2017/0010235 A1 | 1/2017 | Nakamura | |
| 2017/0089852 A1* | 3/2017 | Watanabe | G01N 27/028 |
| 2017/0315082 A1 | 11/2017 | Kawamoto et al. | |

FOREIGN PATENT DOCUMENTS

| | | |
|---|---|---|
| JP | 2015-108583 | 6/2015 |
| JP | 2015-210147 | 11/2015 |
| JP | 2015-219097 | 12/2015 |
| JP | 2016-011885 | 1/2016 |
| WO | 89/03528 | 4/1989 |

* cited by examiner

GAS SENSOR PROVIDED WITH FLANGE PORTION OF COVER THEREOF

CROSS-REFERENCE TO RELATED APPLICATION

This application is based on and claims the benefit of priority from earlier Japanese Patent Application No. 2017-17789 filed Feb. 2, 2017, the description of which is incorporated herein by reference.

BACKGROUND

Technical Field

The present disclosure relates to a gas sensor having a structure that covers a detecting portion of a sensor element.

A gas sensor is disposed in a pipe of an exhaust system of an internal combustion engine and detects an exhaust gas flowing through the pipe as detection gas. The gas sensor performs a gas detection utilizing a change in an oxygen concentration in the detection gas. The usage of the gas sensor includes detection of the oxygen concentration in the exhaust gas exhausted from the internal combustion engine, detection of an air fuel ratio (A/F) of the internal combustion engine from the exhaust gas, detection of whether the A/F obtained from the exhaust gas is a fuel rich side or a fuel lean side with respect to the theoretical A/F value, and detection of specific gases such as NOx.

The gas sensor uses a sensor element having a solid electrolyte and a pair of electrodes. The sensor element is provided with a detecting portion where the detection gas is lead to one of electrodes to perform the gas detection. The sensor element is supported by an insulator having insulation properties in a state where the detecting portion is protruded therefrom. The insulator is supported in a housing which is attached to the exhaust pipe or the like. In the housing, a cover is attached covering the detecting portion of the sensor element to prevent the sensor element from being exposed to the water. In the cover, through holes are formed to allow the detection gas to flow into the detecting portion.

Also, the cover is constituted to have a double structure including an inside cover and an outside cover, to make the detecting portion of the sensor element less exposed to the water. For example, Japanese patent application laid-open publication number 2015-210147 discloses a gas sensor in which a flange portion of an inner cover is supported between the housing and the insulator and the inner cover and the outer cover are fixed by a welding portion. Then, the welding portion is formed in a shape expanded towards the outer periphery, whereby heat of the exhaust gas propagated to the welding portion can be radiated to the housing.

Further, Japanese patent application laid-open publication number 2015-210146 discloses a gas sensor in which a flange portion of an inner cover is supported between the housing and the insulator while a convex portion provided in either one of the inner cover or the housing is protruded into the other one. Hence, the positional relationship between the housing and the inner cover is prevented from being displaced. Also, the patent document (Japanese patent application laid-open publication number 2015-210146) discloses that the flange portion of the inner cover and the flange portion of the outer cover may be supported between the housing and the insulator.

In recent years, the thermal environment has become more severe in the exhaust system to which a gas sensor is mounted. For example, in the case where the gas sensor is mounted upstream of the supercharger, the thermal shock to the gas sensor becomes large, since the gas sensor is likely to be rapidly heated in addition to the fact that the maximum temperature of the exhaust gas is higher than other parts. Also, in the case where gas sensors are mounted to a vehicle adapted for an idling stop or a hybrid vehicle, the engine is frequently stopped, whereby the gas sensors are easily cooled, so that the thermal shock becomes more significant.

According to a gas sensor disclosed by the above-mentioned patent document, i.e., Japanese patent application laid-open publication number 2015-210147, when the welding portion between the inner cover and the outer cover is exposed to the exhaust gas, thereby being heated to high temperature, the strength of the welding portion is lowered because of fatigue, corrosion or the like. Hence, the lowered strength may cause separation of the inner cover and the outer cover. Similarly, in the gas sensor disclosed in the above-mentioned patent document, i.e., Japanese patent application laid-open publication number 2015-210146, the same problem arises when the inner cover and the outer cover are fixed by welding.

According to a structure disclosed by the patent document 2015-210146, in which flange portion of the inner cover and the flange portion of the outer cover are supported between the housing and the insulator, welding portion can be removed. However, the above patent literature JP-A-2015-210146 does not disclose any method to reduce a load applied to the insulator from a flange portion of the inner cover.

Specifically, the inner cover and the outer cover are formed in the following manner. After forming the inner cover and the outer cover by a drawing process or the like, the flange portion of the inner cover and the flange portion of the outer cover are cut by a punching process or the like to obtain prescribed dimensions. At this time, burrs may be formed at a corner portion in the flange portion of the inner cover and a corner portion in the flange portion of the outer cover because of protrusion in a part of the material. In particular, in the case where burrs are formed on a corner portion that faces the insulator, if there is no ways to control a positional relationship between the flange cover of the inner cover and the flange portion of the outer cover, and a load applied to the insulator from the flange portion of the inner cover becomes large so that the insulator is likely to be broken.

SUMMARY

The embodiment provides a gas sensor in which the inner cover or the outer cover thereof is prevented from separating from the gas sensor during the operation, and the insulator can be prevented from being broken.

A gas sensor as one aspect of the present disclosure includes: a sensor element having a detecting portion exposed to detection gas to perform gas detection; an insulator made of ceramic material, supporting the sensor element in a state where the detecting portion is protruded therefrom, the sensor element being inserted through the insulator; a housing made of metal disposed in an outer periphery of the insulator, supporting the insulator; an inner cover made of metal, covering the detecting portion and having an inner through hole that allows the detection gas to flow therethrough; and an outer cover made of metal, covering the inner cover such that a gas passage through which the detection gas flows is formed between the outer cover and the inner cover and having an outer through hole that allows the detection gas to flow therethrough.

An inner flange portion formed over an entire periphery of an end portion of the inner cover and an outer flange portion formed over an entire periphery of an end portion of the outer cover are supported between the insulator and the housing. A protrusion is formed on a corner portion of the inner flange portion, the corner portion facing the insulator 3 and the protrusion contacting with the insulator. An end face of the inner flange portion and an end face of the outer flange portion are mutually offset.

According to one aspect of the gas sensor, both of the inner flange portion of the inner cover and the outer flange portion of the outer cover are supported between the insulator and the housing. In other words, unlike a case where a flange portion between the insulator and the housing is formed only in the inner cover or the outer cover, the inner cover and the outer cover can reliably be prevented from separating from the gas sensor.

In the case where the flange portion is formed in either one of the inner cover and the outer cover only, as a first cover, the other cover has to be joined the first cover by welding or the like. This joint is required to have enough strength to join the first cover to the other cover so that volume of the joint portion increases.

Therefore, when the conventional gas sensor is heated to high temperature when operating, the strength of the inner cover and the outer cover is significantly lowered at the joint portion thereof, which may cause the inner cover and the outer cover to detach from the gas sensor. On the other hand, according to the above-described gas sensor in which both of the inner flange portion of the inner cover and the outer flange portion of the outer cover are supported between the insulator and the housing, a joint portion having large volume is not necessary. Hence, during the operation, the inner cover and the outer cover can be prevented from separating from the gas sensor.

It is preferable that a joint portion produced by welding or the like is not formed between the inner cylindrical portion of the inner cover and the outer cylindrical portion of the outer cover. However, a small joint portion having a small volume using a welding or the like can be provided between the inner cover and the outer cover to maintain the positional relationship therebetween. The volume of the joint portion can be determined such that a degree of lowered strength during heating is within a specified range that prevents the inner cover and the outer cover from separating from the gas sensor.

According to the above-described gas sensor, although a protrusion is formed to contact with the insulator in the corer portion of the inner flange portion which faces the insulator, the end face of the inner flange portion and the end face of the outer flange portion are mutually offset. Thus, according to the protrusion of the inner flange portion formed on the corner portion that faces the insulator, a load applied to the insulator can be reduced.

More specifically, since the end face of the inner flange portion and the end face of the outer flange portion are mutually offset, the protrusion of the inner flange portion and the protrusion of the outer flange portion are not overlapped from each other, even when the protrusion of the outer flange portion is formed on the corner portion thereof that faces the inner flange portion. In particular, in the case where the inner flange portion and the outer flange portion are supported between the insulator and the housing, the load applied between the insulator and the housing is sometimes set to be larger so as to secure sufficient air tightness therebetween. Even in this case, because of a means for offsetting the end face of the inner flange portion and the end face of the outer flange portion, the insulator can be prevented from being broken.

Thus, according to the above-described aspect of the gas sensor, during the operation, the inner cover and the outer cover is prevented from separating from the gas sensor and the insulator can be prevented from being broken.

It should be noted that contents of the gas detection of the sensor element may include detection of the oxygen concentration of the exhaust gas exhausted by the internal combustion engine, detection of the air-fuel ratio of the internal combustion engine which is calculated from the exhaust gas, detection of whether the air-fuel ratio calculated from the exhausted gas is in a fuel rich side or fuel lean side with respect to the theoretical air-fuel ratio, and detection of specific gas components such as NOx.

Note that reference signs in parenthesis of respective elements shown in one aspect of the present disclosure represent correspondence with the reference signs in the drawings for embodiments, but the respective elements are not limited to contents of the embodiments of the present disclosure.

DETAILED DESCRIPTION OF PREFERRED EMBODIMENTS

With reference to the drawings, preferred embodiments of gas sensors according to the present disclosure will be described.

First Embodiment

Figure 1:
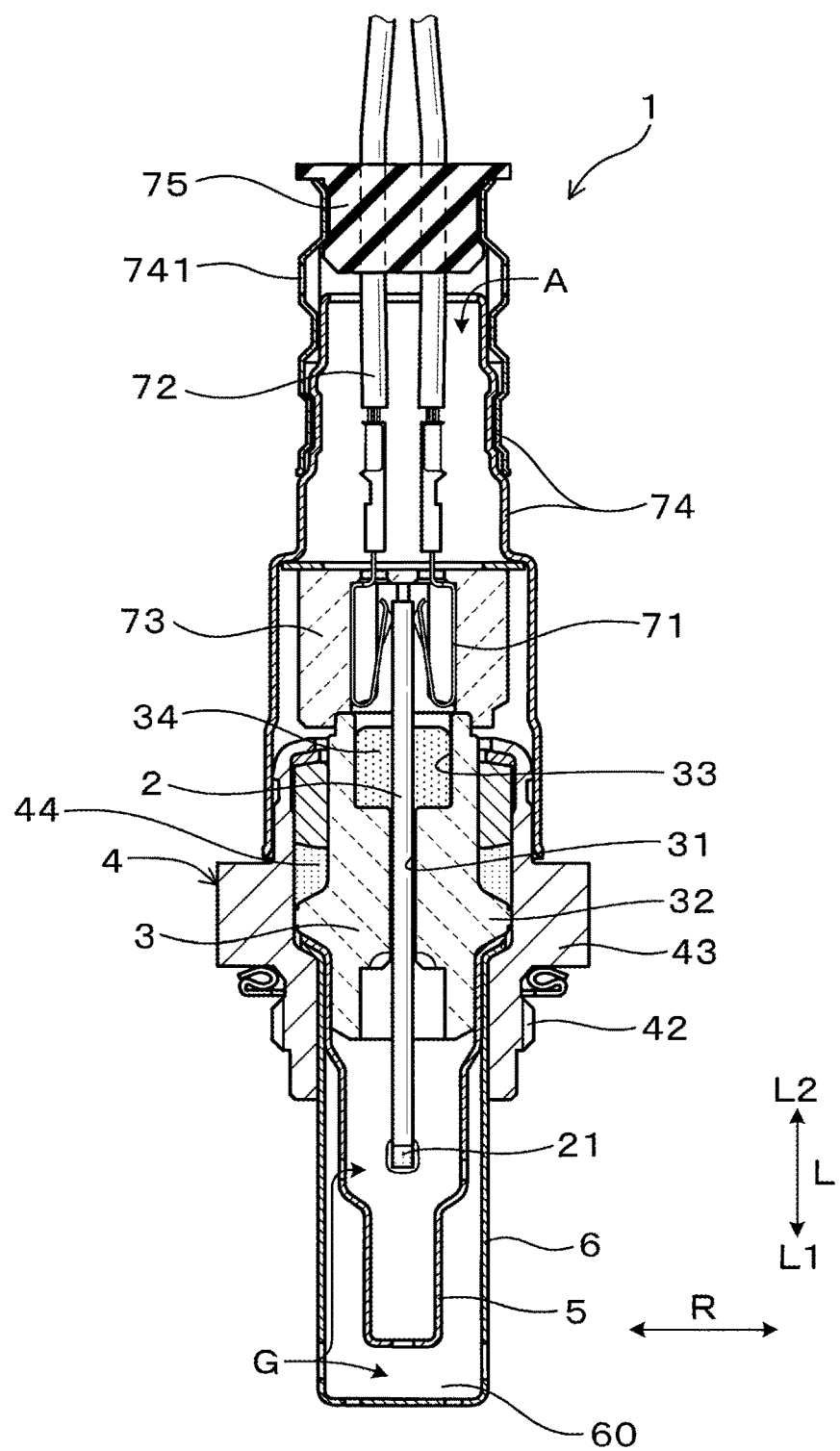
FIG. 1 is a cross-sectional view showing a gas sensor according to a first embodiment of the present disclosure.

As shown in FIG. 1, a gas sensor 1 according to the present embodiment is provided with a sensor element 2, an insulator 3, a housing 4, an inner cover 5 and an outer cover 6. The sensor element 2 includes a detecting portion 21 that is exposed to detection gas G to perform gas detection. The insulator 3 is made of a ceramic material and holds the sensor element 2 in a state where the detecting portion 21 protrudes therefrom, the sensor element 2 being inserted through the insulator 3. The housing 4 is made of metal and disposed in the outer periphery of the insulator 3 and holds the insulator 3.

Figure 2:
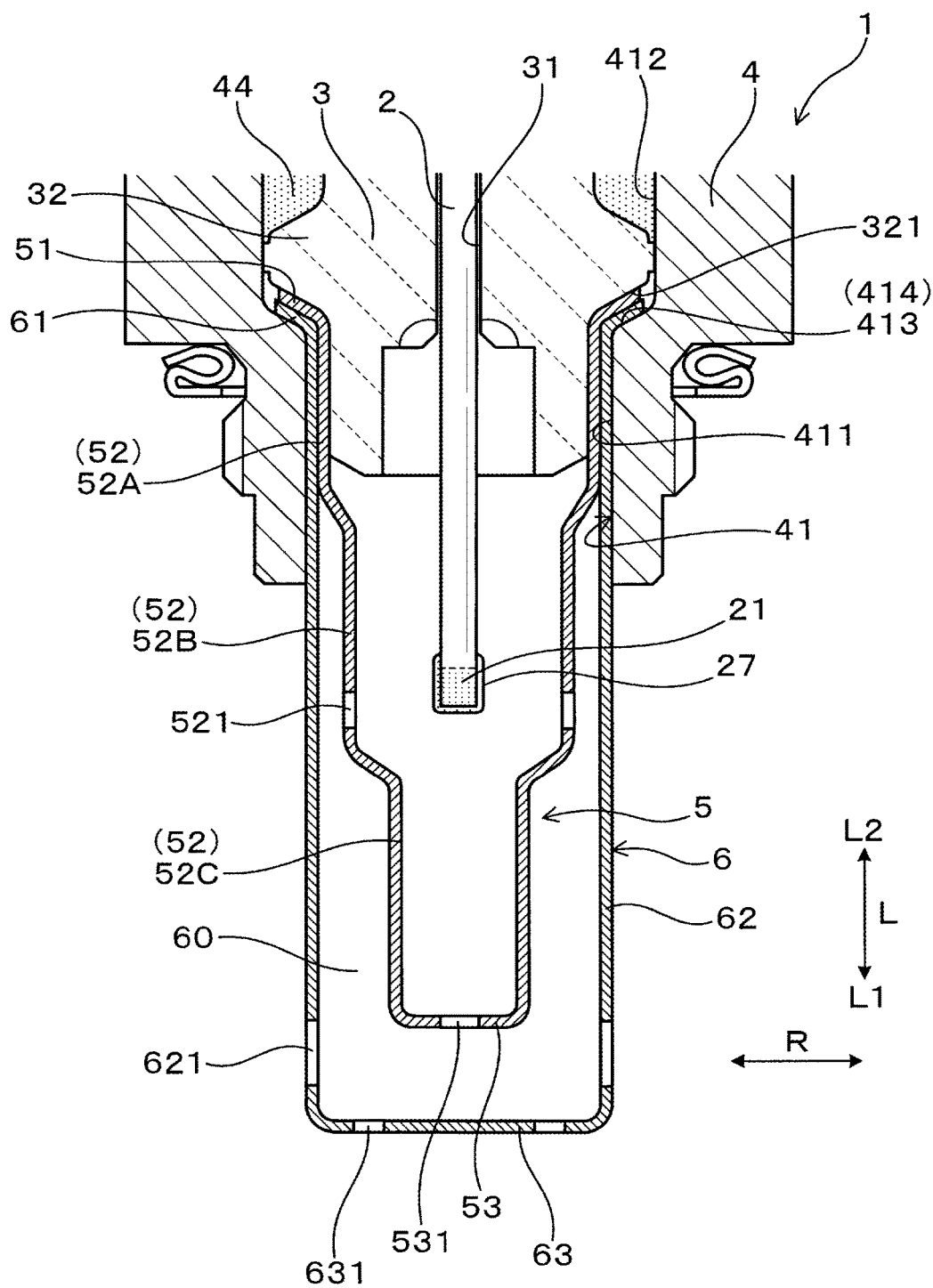
FIG. 2 is an enlarged cross-sectional view showing a part of the gas sensor according to the first embodiment.

As shown in FIG. 2, the inner cover 5 is made of metal. The inner cover 5 covers the detecting portion 21 and has inner through holes 521 and 531. The outer cover 6 is made of metal material. The outer cover 6 covers the inner cover 5 so as to form a gas passage 60 through which the detection gas G flows, and has outer through holes 621 and 631.

Figure 3:
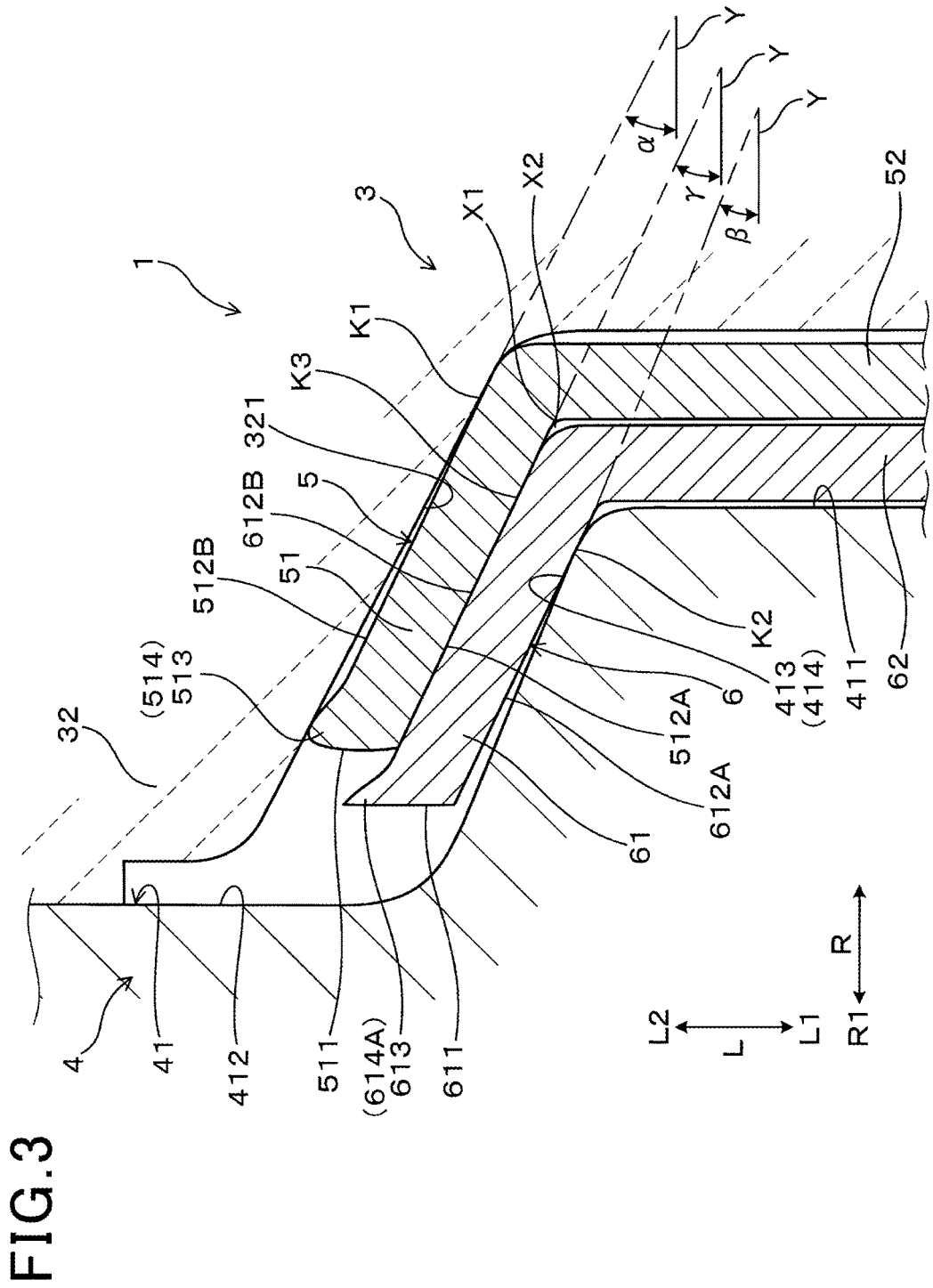
FIG. 3 is a cross-sectional view showing an enlargement of a peripheral portion of an inner flange portion and an outer flange portion supported between an insulator and a housing according to the first embodiment.

As shown in FIG. 3, an inner flange portion 51 formed in the entire circumference of the end portion of the inner cover 5, and an outer flange portion 61 formed in the entire circumference of the end portion of the outer cover 6 are supported between the insulator 3 and the housing 4. In the inner flange portion 51, a protrusion 514 is formed on a corner portion 513 that faces the insulator 3, the protrusion being contacted with the insulator 3. An end face 511 of the inner flange portion 51 and the end face 611 of the outer flange portion 611 are mutually offset. According to the present embodiment, the end face 611 of the outer flange portion 61 is positioned radially closer (in the radial direction R) to an outer side R1 than the end face 511 of the inner flange portion 51 is.

According to the present embodiment, an insertion direction L is defined as a direction through which the sensor element 2 is inserted into the insulator 3. Also, a radial direction R is defined as a direction that orthogonally crosses the insertion direction L and radially extends from a central axis O that passes through the center of the sensor element 2 in the insertion direction L. Further, a direction around the central axis O is defined as a circumferential direction C. A tip end side L1 is defined as a side where the detecting portion 21 protrudes from the sensor element 2, and a rear end side L2 is defined as an opposite side of the tip end side L1.

Hereinafter, the detailed configuration of the gas sensor 1 according to the present embodiment will be described.

Internal Combustion Engine

The gas sensor 1 is disposed in a pipe of an exhaust system (i.e., exhaust pipe) of the internal combustion engine (engine) of a vehicle, and detects oxygen or specific gas in the detection gas G which is an exhaust gas that flows in the exhaust pipe. The gas sensor 1 can be disposed further upstream in the exhaust pipe than a position at which the catalyst is disposed. Moreover, the gas sensor 1 can be disposed further downstream in the exhaust pipe than a position at which the catalyst is disposed. The exhaust pipe in which the gas sensor 1 is disposed can be an intake side pipe of the supercharger that increases the density of air drawn into the internal combustion engine by using the exhaust gas. The pipe in which the gas sensor 1 is disposed can be a pipe in the exhaust gas recirculation mechanism which recirculates a part of the exhaust gas exhausted to the exhaust passage from the internal combustion engine.

A vehicle provided with a pipe to which the gas sensor 1 is disposed may be an ordinary vehicle which travels using gasoline as fuel, a vehicle adapted for idling stop, that is, a vehicle that stops the idling of the internal combustion engine when the vehicle is stopped, a hybrid vehicle or the like. Also, the gas sensor 1 can be used for detecting the oxygen concentration of the exhaust gas from the internal combustion engine, detecting air-fuel ratio (A/F) of the internal combustion engine which is obtained from the exhaust gas, detecting whether the A/F obtained from the exhaust gas is in the fuel rich side or the fuel lean side relative to the theoretical A/F, and detecting specific gas component such as NOx.

Sensor Element 2

Figure 4:
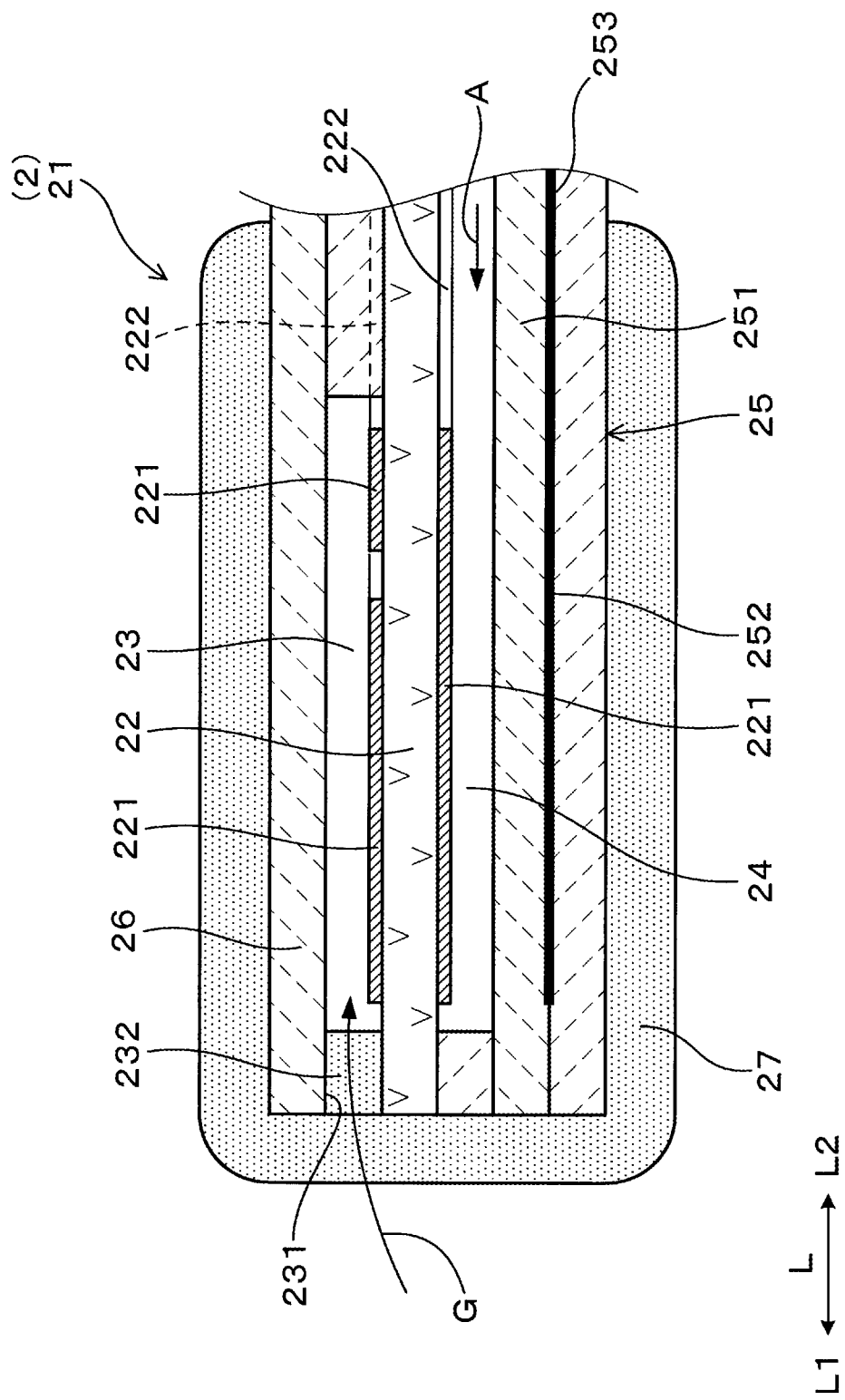
FIG. 4 is a cross-sectional view showing a detecting portion of a sensor element according to the first embodiment.
Figure 5:
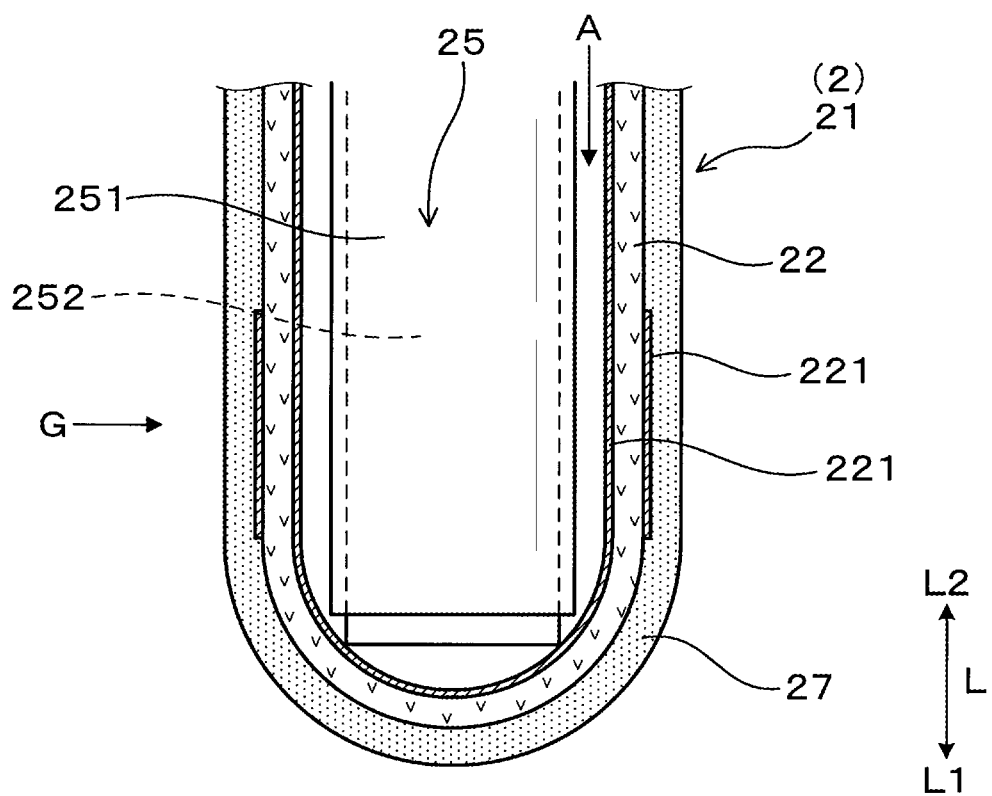
FIG. 5 is a cross-sectional view showing a detecting portion of another sensor element according to the first embodiment.

As shown in FIG. 4, the sensor element 2 includes a solid electrolyte 22 having an ionic conductivity allowing conduction by oxide ion above a predetermined activation temperature, and a pair of electrodes 221 arranged on the surfaces of both sides of the solid electrolyte 22. The sensor element 2 according to the present embodiment is a laminate type element in which a plate-shaped heater 25 is laminated on the plate-shaped solid electrolyte 22. The sensor element 2 may be constituted of a glass type element as shown in FIG. 5, in which a rod-shaped heater 25 is disposed in an inner periphery side of a cup-shaped electrolyte 22. In this case, the electrodes 221 are formed on the inner periphery and the outer periphery of the solid electrolyte 22.

The detection gas G is a target gas from which the gas detection is performed by a detecting portion 21 of the sensor element 2. Note that atmospheric air is used as a reference gas A when performing the gas detection. According to the sensor element 2 which is a laminate type element, the electrode 221 which the detection gas G contacts (the electrode 221 exposed to the detection gas G) is formed on one surface of the plate-shaped electrolyte 22, and the electrode 221 which the reference gas A contacts (the electrode 221 exposed to the reference gas A) is formed on the other surface of the plate-shaped electrolyte. According to the sensor element 2 which is a cup-shaped element, the electrodes 221 which the detection gas G contacts is formed on an outer surface of the glass-shaped electrolyte 22, and the electrode 221 to which the reference gas A touches is formed on an inner surface of the glass-shaped electrolyte 22. The heater 25 in each type of the sensor elements 2 includes a ceramic substrate 251, and a heating element 252 generating heat when being powered, which is disposed on the ceramic substrate 251.

As shown in FIGS. 1 and 2, the sensor element 2 is formed in a shape having the longitudinal side in the insertion direction L along which the sensor element 2 is inserted to the insulator 3. The detecting portion 21 of the sensor element 2 is provided at an end portion of the tip end side L1 in the insertion direction L of the sensor element 2 or in the vicinity of the end portion thereof. In the sensor element 2, a conductor portion 222 connected to the electrodes 221 and a conductor portion 253 connected to the heating element 252 are lead out from an end portion of the rear end side L2 in the insertion direction L. The electrodes 221 and the heating element 252 are connected to an external control circuit or the like via a connection terminal 71 and a lead wire 72.

As shown in FIG. 4, the detecting portion 21 is formed as a portion in which electrodes 221 are provided. The electrodes 221 exposed to the detection gas G is disposed in a gas chamber 23 which is surrounded by the ceramic substrate 26 having insulation properties laminated on the solid electrolyte 22. An introduction port 231 communicates with the gas chamber 23. The introduction port 231 includes a diffusion resistance layer 232 to introduce the detection gas G to the gas chamber 23 at a predetermined diffusion rate. A portion of the tip end side L1 in the insertion direction of the sensor element 2 is covered by a protection layer 27. The diffusion resistance layer 232 and the protection layer 27 are formed of a ceramic porous body. The sensor element 2 includes a duct 24 formed therein, the duct 24 introducing a reference gas A to the electrodes 221 exposed to the reference gas A. The duct 24 is formed, in the insertion direction L of the sensor element 2, from the end portion of the rear end side L2 to a position of the detecting portion 21 where the electrodes 221 are disposed.

Other Sensor Element 2

Figure 6:
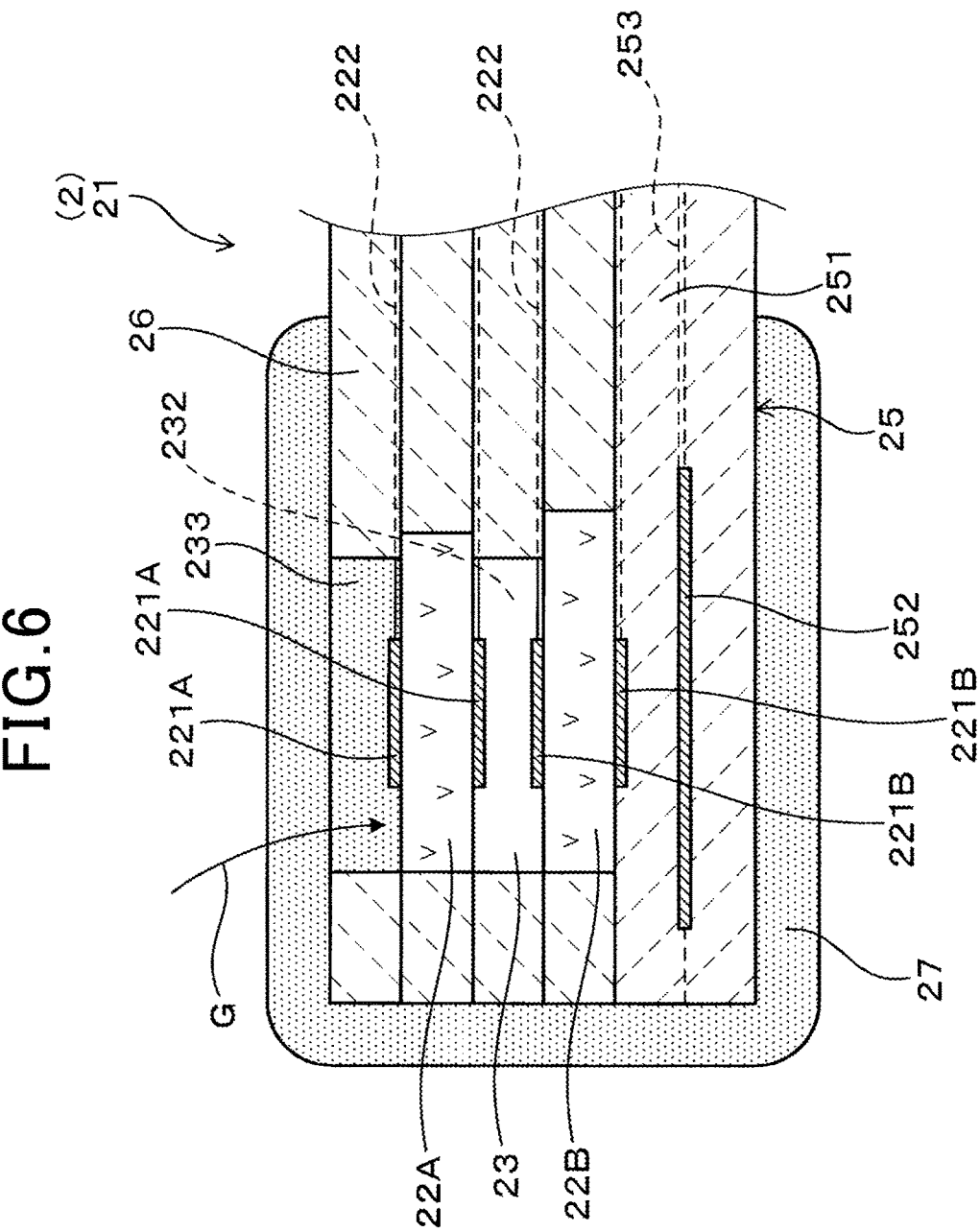
FIG. 6 is a cross-sectional view showing a detecting portion of another sensor element according to the first embodiment.

As shown in FIG. 6, the sensor element 2 can be formed by using two solid electrolytes 22A and 22B, in which a pair of electrodes 221 are provided to each of the solid electrolytes 22A and 22B. In this case, the gas chamber 23 is formed between the two solid electrolytes 22A and 22B to introduce the detection gas G. The gas chamber 23 is formed to be surrounded by the ceramic substrates 226 having insulation properties. A pair of pump electrodes 221A are formed on both sides of a first solid electrolyte 22A to adjust the oxygen concentration of the detection gas G in the gas chamber 23, the pump electrodes being provided to face each other via the first solid electrolyte 22A. One pump electrode 221A is disposed in the gas chamber 23 and the other pump electrode 221A is embedded to a gas introduction layer 233 formed of a porous body through which the detection gas G permeates.

A pair of pump electrodes 221B are formed on both sides of a second solid electrolyte 22B to adjust the oxygen concentration of the detection gas G in the gas chamber 23, the pump electrodes 221B being provided to face each other via the second solid electrolyte 22B. One pump electrode 221B is disposed in the gas chamber 23 and the other pump electrode 221B is embedded to a ceramic substrate 251. A detection cell is formed by the pair of detection electrodes 221B and a part of the second solid electrolytes 22B disposed between the detection electrodes 221B. Also, the diffusion resistance layer 232 is provided in a position adjacent to the gas chamber 23, to introduce the detection gas G at a predetermined diffusion rate. The heater 25 is laminated on each of the solid electrolytes 22A and 22B. The heater 25 includes the ceramic substrate 251, and the heating element 252 provided in the ceramic substrate 251, generating heat when being powered.

Insulator 3

As shown in FIG. 1, the insulator 3 is made of a ceramic having insulation properties. The insulator 3 has an alignment hole 31 to place the sensor element 2 in the insulator 3. The alignment hole 31 penetrates the insulator 3 towards the insertion direction L. The sensor element 2 is inserted through the alignment hole 31 and fixed to the insulator 3 by a glass member 34 or the like which is filled in a concave portion 33 that communicates through the rear end side L2 of the alignment hole 31.

As shown in FIGS. 2 and 3, a support portion 32 is formed in the entire outer periphery of the insulator 3, which is supported in the inner periphery of the housing 4. An insulator opposing surface 321 that faces the inner flange portion 51 is formed on a surface in the tip end side L1 of the support portion 32. The insulator opposing surface 321 is formed to be inclined such that the position of the insulator opposing surface 321 with respect to the insertion direction L becomes closer to the rear end side L2, as the position of insulator opposing surface 321 with respect to the radial direction R becomes closer to the outer side R1 in the radial direction R. In other words, the insulator opposing surface 321 has a tapered shape such that the diameter thereof increases towards the rear end side L2 from the tip end side L1 in the insertion direction L.

Housing 4

As shown in FIGS. 2 and 3, the housing 4 has a support hole 41 extending in the insertion direction L to dispose the insulator 3. The support hole 41 includes a small hole portion 411 positioned in the tip end side L1 in the insertion direction L, and a large hole portion 412 having a diameter larger than that of the small hold portion 411, positioned in the rear end side L2 in the insertion direction L2. The insulator 3 is inserted through the small hole portion 411 and the large hole portion 412 of the support hole 41, and fixed to the housing 4 by bending the end portion of the housing 4 in the rear end side L2 in the insertion direction L, using talc powder and a sealing member 44 such as a sleeve seal provided in the large hole portion 412.

A step portion 413 is formed in the entire circumference space between the small hole portion 411 and the large hole portion 412. The step portion 413 has a housing opposing surface 414 that faces the outer flange portion 61. The housing opposing surface 414 is formed to be inclined such that the position of the housing opposing surface 414 with respect to the insertion direction L becomes closer to the rear end side L2, as the position of housing opposing surface 414 with respect to the radial direction R becomes closer to the outer side R1 in the radial direction R. In other words, the housing opposing surface 414 has a tapered shape such that the diameter thereof increases towards the rear end side L2 from the tip end side L1 in the insertion direction L. Also, as shown in FIG. 1, a screw portion 42 and a flange portion 43 are formed on the entire outer periphery of the housing 4 so as to mount the gas sensor 1 which is inserted into a mount hole provided to the pipe.

Rear End Side Insulator 73

As shown in FIG. 1, a rear end side insulator 73 is disposed in the rear end side L2 of the insulator 3 in the insertion direction L, thereby supporting the connection terminal 71 which is electrically connected to the conductor portion 222 of the electrodes 221 or the conductor portion 253 of the heating element 252. Further, in the housing 4, a wiring cover 74 is disposed in a portion closer to the rear end side L2 than the position of the flange portion 43 in the insertion direction L, to cover the rear end side insulator 73, the connection terminal 71 and the lead wire 72 or the like. The lead wire 72 is supported by a bush 75 disposed in the wiring cover 74. The wiring cover 74 has an introduction port 741 formed therein, for introducing atmospheric air as the reference gas A. The atmospheric air introduced from the introduction port 741 is lead to the duct 24 of the sensor element 2 through the gap in the wiring cover 74 and the rear end side insulator 73.

Inner Cover 5 and Outer Cover 6

As shown in FIG. 2, the inner cover 5 includes an inner cylindrical portion 52 formed in a cylindrical shape along the insertion direction L, and an inner bottom portion 53 formed at an end portion of the inner cylindrical portion 52 in the tip end side L1 in the insertion direction L. For the inner through holes 521 and 531 through which the detection gas G passes, a plurality of inner through holes 521 are formed at plural positions of the inner cylindrical portion 52 in the circumferential direction C, the inner through hole 531 is formed at the inner bottom portion 53. The inner cylindrical portion 52 includes a first inner cylindrical portion 52A attached to the outer periphery of the insulator 3, a second inner cylindrical portion 52B being extended from the tip end side of the first inner cylindrical portion 52A in the insertion direction L, having smaller diameter than that of the first inner cylindrical portion 52A, and a third inner cylindrical portion 52C being extended from the tip end side of the second inner cylindrical portion 52B in the insertion direction L, having smaller diameter than that of the second inner cylindrical portion 52B. The detecting portion 21 of the sensor element 2 is disposed in the second inner cylindrical portion 52B.

The inner flange portion 51 is formed in the rear end portion of the first inner cylindrical portion 52A in the insertion direction L such that the inner flange portion 51 is bent towards the outer side R1 in the radial direction R. The inner flange portion 51 is formed to be inclined such that the position of the inner flange portion 51 with respect to the insertion direction L becomes closer to the rear end side L2, as the position of inner flange portion 51 with respect to the radial direction R becomes closer to the outer side R1 in the radial direction R. In other words, the inner flange portion 51 has a tapered shape such that the diameter thereof increases towards the rear end side L2 from the tip end side L1 in the insertion direction L.

The outer cover 6 includes an outer cylindrical portion 62 formed in a cylindrical shape along the insertion direction L, and an outer bottom portion 63 formed in an end portion of the outer cylindrical portion 62 in the insertion direction L. For the outer through holes 621 and 631 through which the detection gas G passes, a plurality of outer through holes 621 are formed at plural positions of the outer cylindrical portion 62 in the circumferential direction C, and a plurality of inner through holes 631 are formed at plural positions of the outer bottom portion 63.

The outer flange portion 61 is formed in the rear end portion of the outer cylindrical portion 62 in the insertion direction L such that the outer flange portion 61 is bent towards the outer side R1 in the radial direction R. The outer flange portion 61 is formed to be inclined such that the position of the outer flange portion 61 with respect to the insertion direction L becomes closer to the rear end side L2, as the position of the outer flange portion with respect to the radial direction R becomes closer to the outer side R1 in the radial direction R. In other words, the outer flange portion 61 has a tapered shape such that the diameter thereof increases towards the rear end side L2 from the tip end side L1 in the insertion direction L.

As shown in FIG. 2, the gas passage 60 between the inner cover 5 and the outer cover 6 is formed continuously between the inner cylindrical portion 52 of the inner cover 5 and the outer cylindrical portion 62 of the outer cover 6, and the inner bottom portion 53 of the inner cover 5 and the outer bottom portion 63 of the outer cover 6. A part of the detection gas G flowing from the pipe of the internal combustion flows inside the outer cover 6 by passing through the outer through holes 621 and 631, and flows inside the inner cover 5 by passing through the gas passage 60 and the inner through holes 521. Then, this detection gas G contacts the detecting portion 21 of the sensor element 2 inside the inner cover 5, and flows into the gas passage 60 by passing through the inner through hole 531 from inside the inner cover 5. Further, the detection gas G flows outside the outer cover 6 by passing the outer through holes 621 and 631 from the gas passage 60.

The inner cover 5 and the outer cover 6 are arranged in the pipe, whereby the detection gas G may flow into a gap formed between the support hole 41 of the housing 4 and the outer cylindrical portion 62 of the outer cover 6, a gap between the outer cylindrical portion 62 of the outer cover 6 and the inner cylindrical portion 52 of the inner cover 5, and a gap between the inner cylindrical portion 52 of the inner cover 5 and the outer periphery of the insulator 3. Also, the pressure inside the pipe is higher than atmospheric pressure. Hence, by keeping air tightness at the inner flange portion 51 and the outer flange portion 61 which are positioned (supported) between the insulator opposing surface 321 and the housing opposing surface 414, the detection gas G flowing into the respective gaps can be prevented from deeply entering inside the support hole 41, and also prevented from being mixed with atmospheric air which is the reference gas A that flows through the duct 24 of the sensor element 2.

The detection portion 21 of the sensor element 2 utilizes a difference between the oxygen concentration in the reference gas A and the oxygen concentration in the detection gas G to perform gas detection. Therefore, if the detection gas G is mixed with the reference gas A which is the reference for the gas detection, the accuracy of the gas detection is deteriorated. Hence, in order to maintain the accuracy of the gas detection, a gap between the insulator opposing surface 321 and the housing opposing 414 is occluded so as to prevent the detection gas G from entering into the gas sensor 1 through the gap.

As shown in FIG. 3, a boundary portion K1 between the insulator opposing surface 321 and the surface 512B of the inner flange portion 51 positioned in the rear end side L2 in the insertion direction L is closed by a protrusion 514. A boundary portion K2 between the housing opposing surface 414 and the surface 612A of the outer flange portion 61 positioned in the tip end side L1 in the insertion direction L is closed by these surfaces 414 and 612A when being contacted with each other. Similarly, a boundary portion K3 between the surface 512A of the inner flange portion 51 positioned in the tip end side L1 in the insertion direction L and the surface 612B of the outer flange portion 61 positioned in the rear end side L2 in the insertion direction is closed by these surfaces 512A and 612B when being contacted with each other.

The burr 614A of the outer flange portion 61 is formed as a protrusion which does not contact with the inner flange portion 51. The end face 611 of the outer flange portion 61 is positioned radially closer to the outer side R1 than the end face 511 of the inner flange portion 51 is, and positioned in a portion where the burr 614A as the protrusion does not contact with the inner flange portion 51. Thus, the protrusion 514 and the burr 614A are not overlapped in the insertion direction L.

The inner cover 5 and the outer cover 6 are formed of stainless steel having high corrosion resistance. The inner cover 5 and the outer cover 6 according to the present embodiment is formed of SUS310S. When using the same material for the inner cover 5 and the outer cover 6, since electrical properties are the same between the inner cover 5 and the inner cover 6, potential difference is unlikely to occur therebetween. Hence, the corrosiveness of these materials can be improved. For the inner cover 5 and the outer cover 6, a metal material having good corrosiveness other than the stainless steel can be used.

The materials for the inner cover 5 and the outer cover 6 may be the same or different. When the burr 614A of the outer flange portion 61 is plastically deformed by the inner flange portion 51, the rigidity of the outer flange portion 61 can be set to be lower than that of the inner flange portion 51. In this case, the burr 614A can be plastically deformed easily.

Inner Flange Portion 51 and Outer Flange Portion 61

As shown in FIG. 2, the inner through hole 521 of the inner cylindrical portion 52 and the outer through hole 621 of the outer cylindrical portion 62 are formed to be offset each other in the insertion direction L. The inner through hole 531 of the inner bottom portion 53 and the outer through hole 631 of the outer bottom portion 63 are offset each other in the radial direction R. The first inner cylindrical portion 52A of the inner cylindrical portion 52, positioned in the rear end side L2 in the insertion direction L, is disposed to overlap the inner periphery side of the outer cylindrical portion 62 in the rear end side L2 in the insertion direction L. The inner flange portion 51 is disposed to overlap the rear end side L2 of the outer flange portion 61 in the insertion direction L.

As shown in FIG. 3, the length from a bending point X2 in the inner periphery side of the outer flange portion 61, which is bending from the outer cylindrical portion 62, to the end face 611 is longer than a length from a bending point X1 in the outer periphery side of the inner flange portion 51, which bends from the inner cylindrical portion 52, to the end face 511. The end face 611 of the outer flange portion 61 is positioned further radially outwards than the end face 511 of the inner flange portion 51 is. The distance from the end face 511 of the inner flange portion 51 to the end face 611 of the outer flange portion 61 may preferably be in a range from 0.1 to 5.0 mm. When the distance is less than 0.1 mm, the burr 514A of the inner flange portion 51 and the burr 614A of the outer flange portion 61 are likely to overlap in the insertion direction L. On the other hand, when the distance exceeds 5.0 mm, the end face 511 of the inner flange portion 51 and the end face 611 of the outer flange portion 61 are significantly separated from each other, so that either the inner flange portion 51 or the outer flange portion 61 has to be formed shorter. This is not favorable.

Here, the bending point X1 refers to a point at which a virtual line drawn along the outer periphery surface of the inner cylindrical portion 52 in the insertion direction L, and a virtual line drawn along the surface 512A in the tip end side L1 of the inner flange portion 51 cross each other, in a cross section of the inner cover 5 and the outer cover 6 taken along the insertion direction L. The bending point X2 refers to a point at which a virtual line drawn along the inner periphery surface of the outer cylindrical portion 62 in the insertion direction L, and a virtual line drawn along the surface 612B in the rear end side L2 of the outer flange portion 61 are crossed each other, in a cross section of the inner cover 5 and the outer cover 6 taken along the insertion direction L. Also, the end face 511 of the inner flange portion 51 refers to a tip end face positioned in the outer side R1 of the inner flange portion 51 in the radial direction. The end face 611 of the outer flange portion 61 refers to a tip end face positioned in the outer side R1 of the outer flange portion 61 in the radial direction.

The thickness of the outer flange portion 61 and the inner flange portion 51 may preferably be within a range from 0.2 mm to 2.0 mm. In the case where the thickness is less than 0.2 mm, the strength of the outer flange portion 61 or the inner flange portion 51 is insufficient. On the other hand, when the thickness is larger than 2.0 mm, pressing or the like of the outer flange portion or the inner flange portion is difficult to achieve.

The height of the protrusion 514 formed on the corner portion 513 in the rear end side L2 of the inner flange portion 51 in the insertion direction L may be larger than or equal to 0.05 mm from the surface 512B. However, in the case where the height is larger than or equal to 0.05 mm, a problem arises that a load applied to the insulator 3 becomes larger when the burr 514A of the inner flange portion 51 and the burr 614A of the outer flange portion 61 are overlapped in the insertion direction L.

Figure 7:
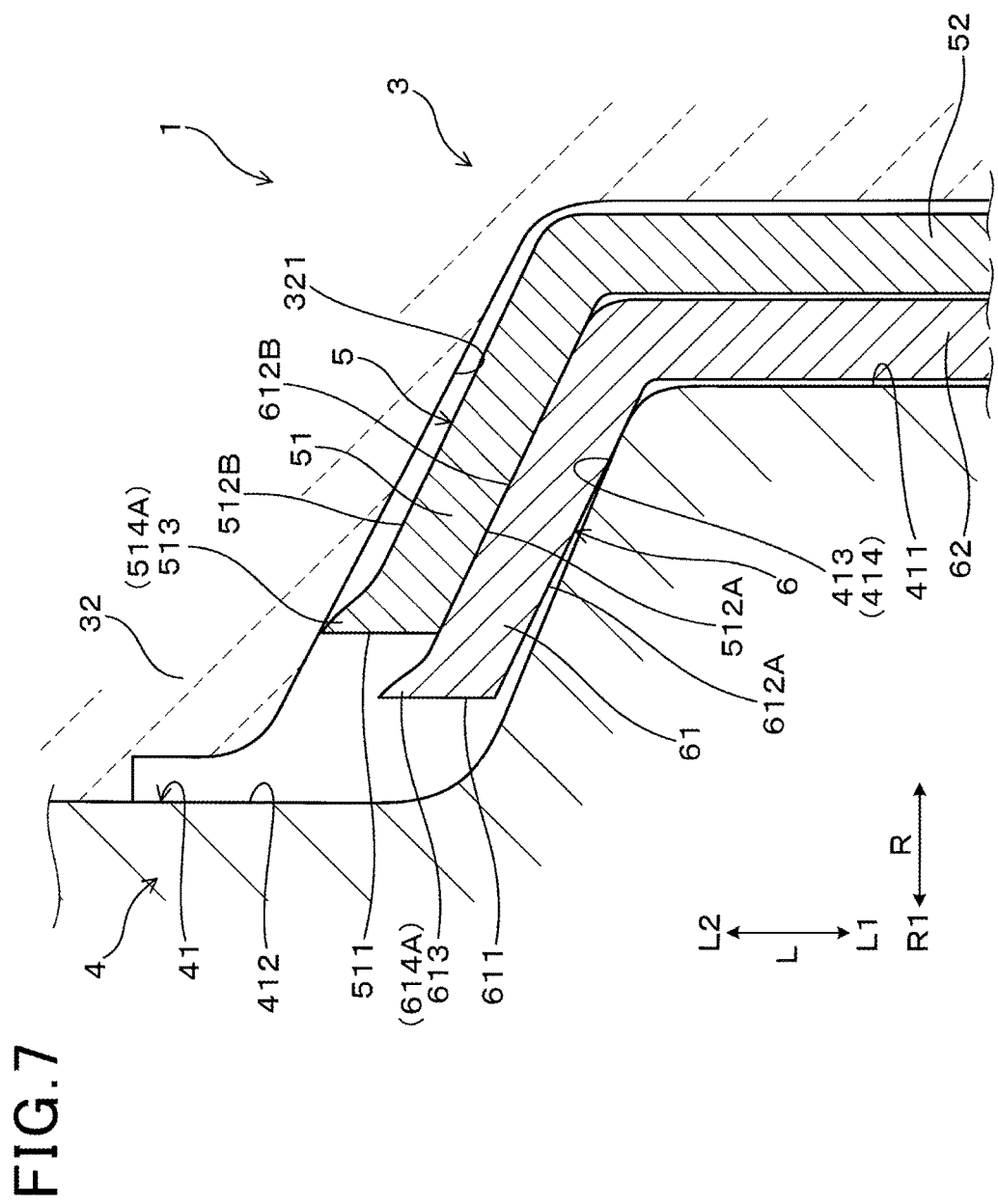
FIG. 7 is an enlarged cross-sectional view showing a peripheral portion of the inner flange portion and the outer flange portion before being supported between the insulator and the housing according to the first embodiment.

As shown in FIG. 7, in an initial state of the inner cover 5 and the outer cover 6 before assembling the gas sensor 1, the end face 511 of the inner flange portion 51 is formed approximately parallel to the insertion direction L, and also the end face 611 of the outer flange portion 61 is formed approximately parallel to the insertion direction L.

The end face 511 of the inner flange portion 51 can be formed to be approximately parallel to the insertion direction L, by cutting a portion to be formed as the inner flange portion 51 in the insertion direction L, after shaping the inner cover 5 by drawing or the like. The inner flange portion 51 of the inner cover 5 of the present embodiment is cut from the tip end side L1 towards the rear end side L2 in the insertion direction L, and the burr 514A, where a part of the material is protruded, is formed on the corner portion 513 of the inner flange portion 51 in the rear end side L2 in the insertion direction L when the inner flange portion 51 is.

Similarly, the end face 611 of the outer flange portion 61 can be formed to be approximately parallel to the insertion direction L, by cutting a portion to be formed as the inner flange portion 61 in the insertion direction L, after shaping the outer cover 6 by drawing or the like. The inner flange portion 61 of the inner cover 6 of the present embodiment is cut from the tip end side L1 towards the rear end side L2 in the insertion direction L, and the burr 614A, where a part of the material is protruded, is formed on the corner portion 613 of the inner flange portion 61 in the rear end side L2 in the insertion direction L when the inner flange portion 61 is cut.

When the inner flange portion 51 and the outer flange portion 61 are disposed between the insulator opposing surface 321 and the housing opposing surface 414, the end portion of the inner flange portion 51 and the end face of the outer flange portion 61 are appropriately plastically deformed. After assembling the gas sensor 1, the end face 511 of the inner flange portion 51 and the end face 611 of the outer flange portion 61 may be inclined with respect to the insertion direction L, or may be bent to have curved surfaces.

The end face 511 of the inner flange portion 51 may be formed in a direction substantially orthogonal to a direction along which the inner flange portion 51 is formed. Also, the end face 511 of the inner flange portion 51 is not necessary formed in a flat shape, but may be formed in a curved surface shape having a convex or concave shape, an uneven shape, or a shape in which a part of the shape is expanded. Similarly, the configuration of the end face 611 of the outer flange portion 51 is the same as that of the end face 511 of the inner flange portion 51.

Figure 8:
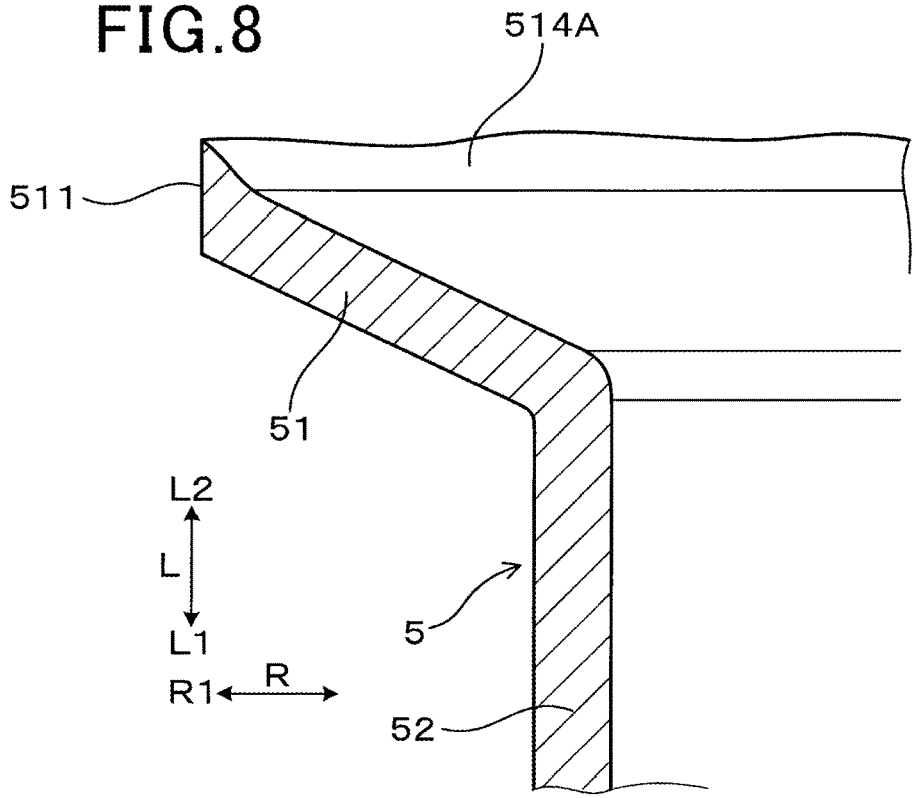
FIG. 8 is a diagram illustrating a state of a burr formed in a corner portion of an inner flange portion according to a first embodiment.
Figure 9:
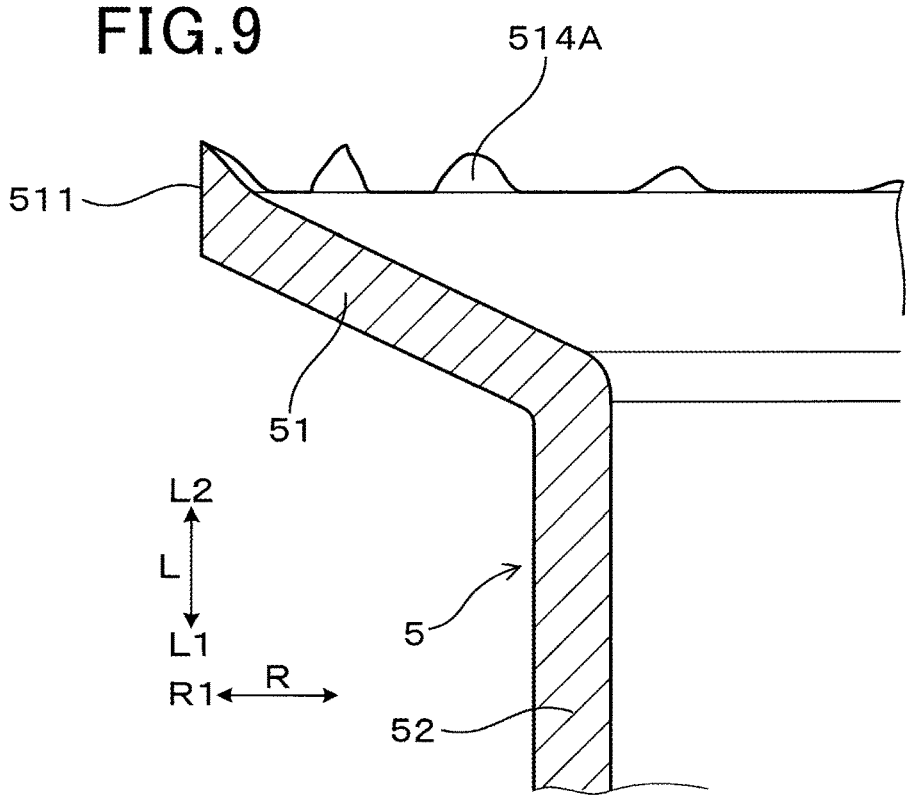
FIG. 9 is a diagram illustrating a state of a burr formed in a corner portion of another inner flange portion according to the first embodiment.

The burr 514A in the corner portion 513 of the inner flange portion 51 is formed when cutting or the like is performed. Hence, various shapes can be possible for the burr 514A. For example, as shown FIG. 8, the burr 514A may be formed in the entire periphery in the circumferential direction C of the corner portion 513 of the inner flange portion 51. Also, the burr 514A may be formed irregularly in a part of the corner portion 513 in the circumferential direction C.

Inclination angle α, β, γ

As shown in FIG. 3, according to the gas sensor 1 of the present embodiment, the inclination angles α, β, γ respective portions of the insulator 3 and the housing 4 which supports the inner flange portion 51 and the outer flange portion 61 are appropriately considered.

Specifically, the inclination angles α, β, γ are formed to be different from each other. That is, the inclination angle α of the insulator opposing surface 321 in the support portion 32 of the insulator 3, with respect to a virtual reference line Y which is parallel to the radial direction; the inclination angle β of the housing opposing surface 141 formed at the step portion 413 in the support hole 41 of the housing 4, with respect to a virtual reference line Y which is parallel to the radial direction R; and the inclination angle γ of the inner flange portion 51 and the outer flange portion 61, with respect to a virtual reference line Y which is parallel to the radial direction R, are different. Note that inclination angles α, β, γ are slightly different from each other, however, the difference among the inclination angles α, β, γ are illustrated with exaggeration.

According to the present embodiment, the inclination angle γ of the inner flange portion 51 and the outer flange portion 61 is larger than or equal to the inclination angle β of the housing opposing surface 414, and smaller than the inclination angle α of the insulator opposing surface 321. In other words, a relationship of β<γ≤α is satisfied according to the gas sensor 1 of the present embodiment. With this configuration, a load applied to the insulator opposing surface 321 can be reduced while the air tightness between the insulator opposing surface 321 and the housing opposing surface 414 is secured.

The inclination angle β of the housing opposing surface 414 is smaller than the inclination angle α of the insulator opposing surface 321, whereby a gap can be formed between the insulator opposing surface 321 and the housing opposing 414 such that the closer to the outer side R1 in the radial direction R (i.e., further outward), the larger the gap is. According to this configuration, when the inner flange portion 51 and the outer flange portion 61 are disposed between the insulator opposing surface 321 and the housing opposing surface 414, the burr 514A of the corner portion 513 in the inner flange portion 51 does not strongly contact with the insulator opposing surface 321.

Since the inclination angle γ of the inner flange portion 51 and the outer flange portion 61 is smaller than the inclination angle α of the insulator opposing surface 321, a gap can be formed between the surface 512B of the inner flange portion 51 in the rear end side L2 and the insulator opposing surface 321 such that the closer to the outer side R1 in the radial direction R, the larger the gap is. Thus, when the inner flange portion 51 and the outer flange portion 61 are disposed between the insulator opposing surface 321 and the housing opposing surface 414, the burr 514A of the corner portion 513 of the inner flange portion 51 is likely to incline, by the insulator opposing surface 321, towards the outer side R1 in the radial direction R.

Assuming the burr 514A inclines towards the inner side R2 in the radial direction R, the burr 514A is strongly compressed between the surface 512B of the inner flange portion 51 and the insulator opposing surface 321. In this case, a load applied to the insulator opposing surface 321 from the burr 514A becomes strong so that the insulator opposing surface 321 is likely to be cracked.

On the other hand, when the burr 514A of the inner flange portion 51 inclines towards the outer side R1 in the radial direction R, the burr 514A may be bent by the insulator opposing surface 321 towards the outer side R1 in the radial direction R. Hence, the load applied to the insulator opposing surface 321 from the burr 514a becomes small so that the insulator opposing surface 321 is unlikely to be cracked.

Figure 10:
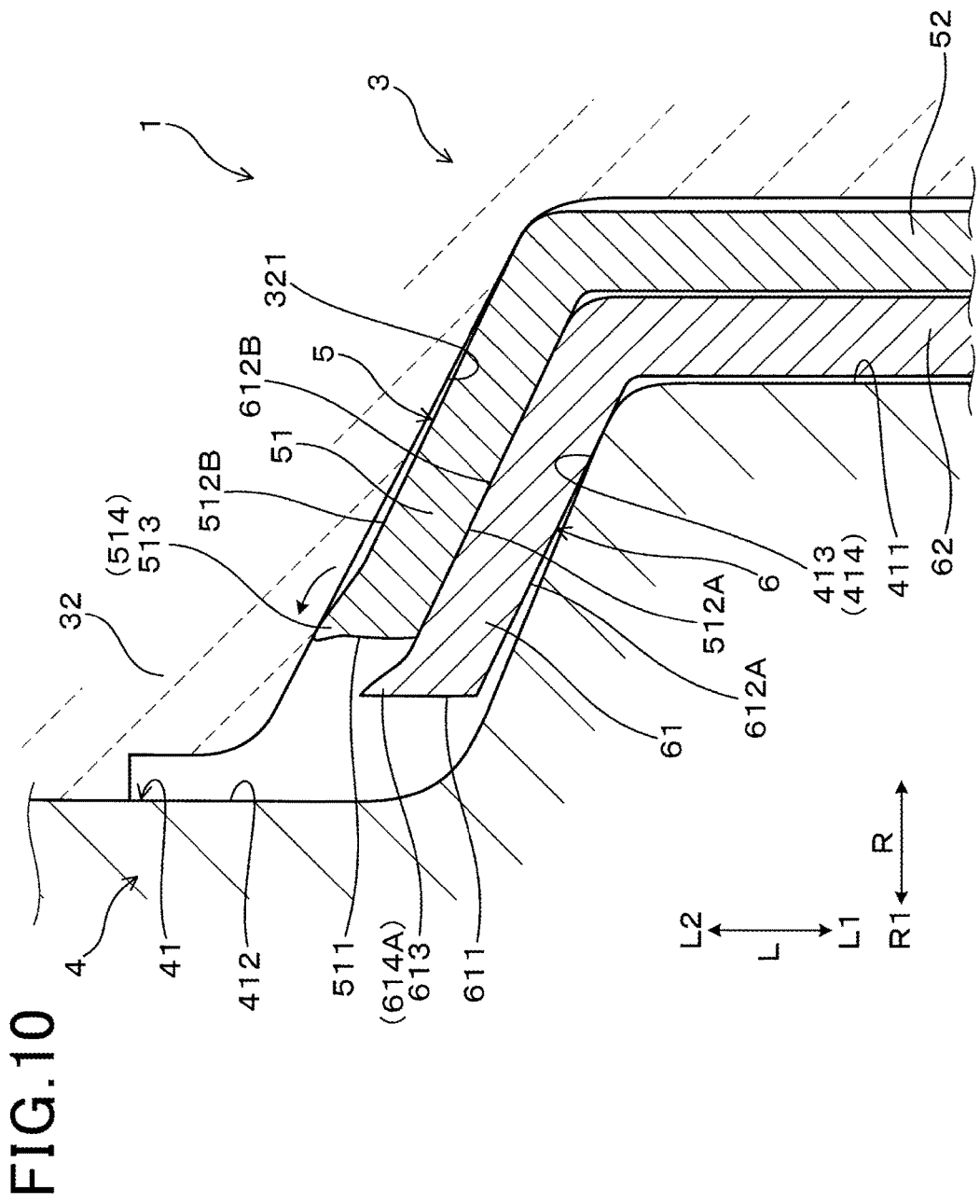
FIG. 10 is a cross-sectional view showing an enlargement of a peripheral portion of another inner flange portion and outer flange portion supported between the insulator and the housing according to the first embodiment.

FIG. 10 simply illustrates a protrusion 513 formed such that the burr 514A of the corner portion 513 in the inner flange portion 51 is plastically deformed by the insulator opposing surface 321 to be inclined towards the outer side R1 in the radial direction R. Since the actual protrusion 513 is influenced by a formation of the burr 514A, a thickness and material type of the inner flange portion 51, a degree of the inclination angles α, β, γ and a difference between the inclination angles α, β, γ, the protrusion 513 may have a round shape shown in FIG. 3, or a sharp shape.

The inclination angle γ of the inner flange portion 51 and the outer flange portion 61 is set between the inclination angle α of the insulator opposing surface 321 and the inclination angle β of the housing opposing surface 414, whereby the insulator opposing surface 321 and the housing opposing surface 414 prevent excessive load from being applied to the inner flange portion 51 and the outer flange portion 61. Then, the burr 514A is appropriately plastically deformed by the insulator opposing surface 321, thereby forming the protrusion 513.

In the gas sensor 1, instead of satisfying the relationship β≤γ<α, a relationship β<γ≤α may be satisfied. This is achieved under a condition that the inclination angle α of the insulator opposing surface 321 is larger than the inclination angle β of the housing opposing surface 414, and the inclination angle γ of the inner flange portion and the outer flange portion 61 may be the same as the inclination angle α of the insulator opposing surface 321 or the inclination angle β of the housing opposing surface 414. At least when the inclination angle α of the insulator opposing surface 321 is larger than the inclination angle β of the housing opposing surface 414, the following effects can be obtained. That is, a load applied to the insulator opposing surface 321 from the burr 514A of the inner flange portion 51 can be reduced.

A difference between the inclination angle α of the insulator opposing surface 321 and the inclination angle β of the housing opposing surface 414 can be set within a range from 0.5° to 10°. In the case where the difference between the inclination angle α and the inclination angle β is small, it is necessary to increase a degree of plastic deformation of the burr 514A of the inner flange portion 51. On the other hand, when the difference between the inclination angle α and the inclination angle β is significantly large, a contact area between the insulator 3, the inner flange portion 51, the outer flange portion 61 and the housing 4 becomes small.

The insulator opposing surface 321 and the opposing surface 414 are appropriately inclined so that appropriate shearing load in addition to a compressive load can be applied between the inner flange portion 51 and the outer flange portion 61. Hence, adhesion strength between the insulator 3, the inner flange portion 51, the outer flange portion 61 and the housing 4 can be enhanced. Each of the inclination angle α of the insulator opposing surface 321, the inclination angle β of the housing opposing surface 414, and the inclination angle γ of the outer flange portion 61 can be set within a range from 5° to 45°, on the assumption that a relationship $\beta \leq \gamma < \alpha$, or a relationship $\beta < \gamma \leq \alpha$ is satisfied.

When respective inclination angles α, β, γ are significantly small, the enhanced adhesion effect in unlikely to obtain between the insulator 3, the inner flange portion 51, the outer flange portion 61 and the housing 4. Meanwhile, when the respective inclination angles α, β, γ are significantly large, the inner flange portion 51 and the outer flange portion 61 is difficult to be supported between the insulator opposing surface 321 and the housing opposing surface 414.

Moreover, after assembling the gas sensor 1, the inner flange portion 51 and the outer flange portion 61 closely contact with each other. Before assembling the gas sensor 1, the inclination angle γ of the inner flange portion 51 and the inclination angle γ are configured to be the same. However, the inclination angle γ of the inner flange portion 51 and the inclination angle γ may be different, before assembling the gas sensor 1. In this case, since the inner flange portion 51 and the outer flange portion 61 are closely contacted with each other, when being supported between the insulator opposing surface 321 and the housing opposing surface 414, the inclination angle γ of the inner flange portion 51 and the inclination angle γ of the outer flange portion become the same.

Alignment of Positional Offset

Figure 11:
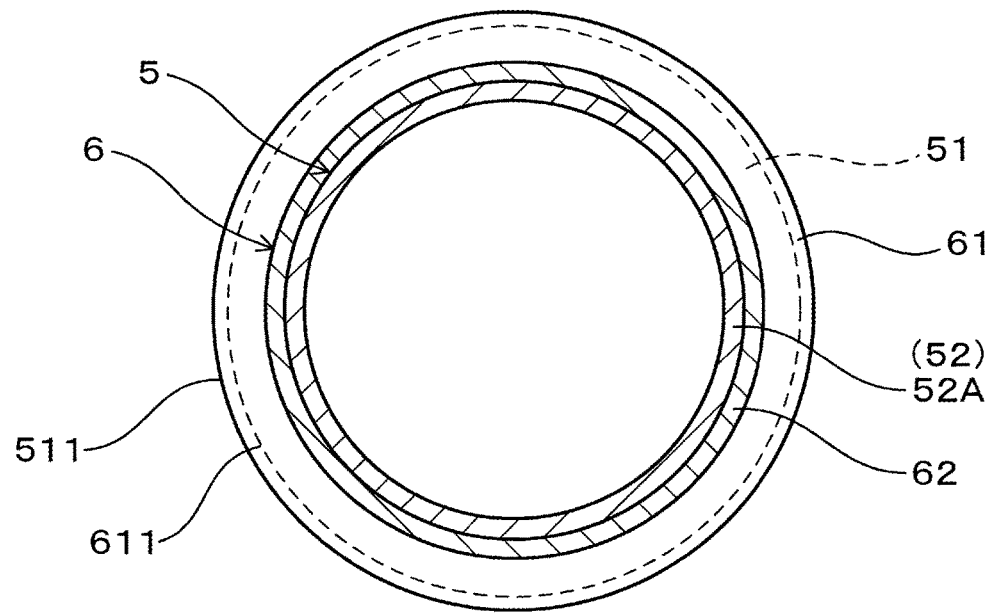
FIG. 11 is an explanatory diagram showing the inner flange portion and the outer flange portion according to the first embodiment, when seen from a tip end portion of the sensor element in the insertion direction thereof.

As shown in FIG. 11, according to the present embodiment, mutual positions between the end face 511 of the inner flange portion 51 and the end face 611 of the outer flange portion 61 are offset such that the end face 611 of the entire periphery in the circumferential direction C of the outer flange portion 61 is positioned to be in the outer side R1 than the end face 511 of the entire periphery in the circumferential direction C of the inner flange portion 51. In other words, the positional offset is accomplished such that the center axis line of the inner cover 5 passing through the center of the inner cylindrical portion 52 and the inner bottom portion 53 in the insertion direction L, and the center axis line of the outer cover 6 passing through the center of the outer cylindrical portion 62 and the outer bottom portion 63 are coincident, and the length of the outer flange portion 61 is longer than that of the inner flange portion 51 over the entire periphery in the circumferential direction C.

Figure 12:
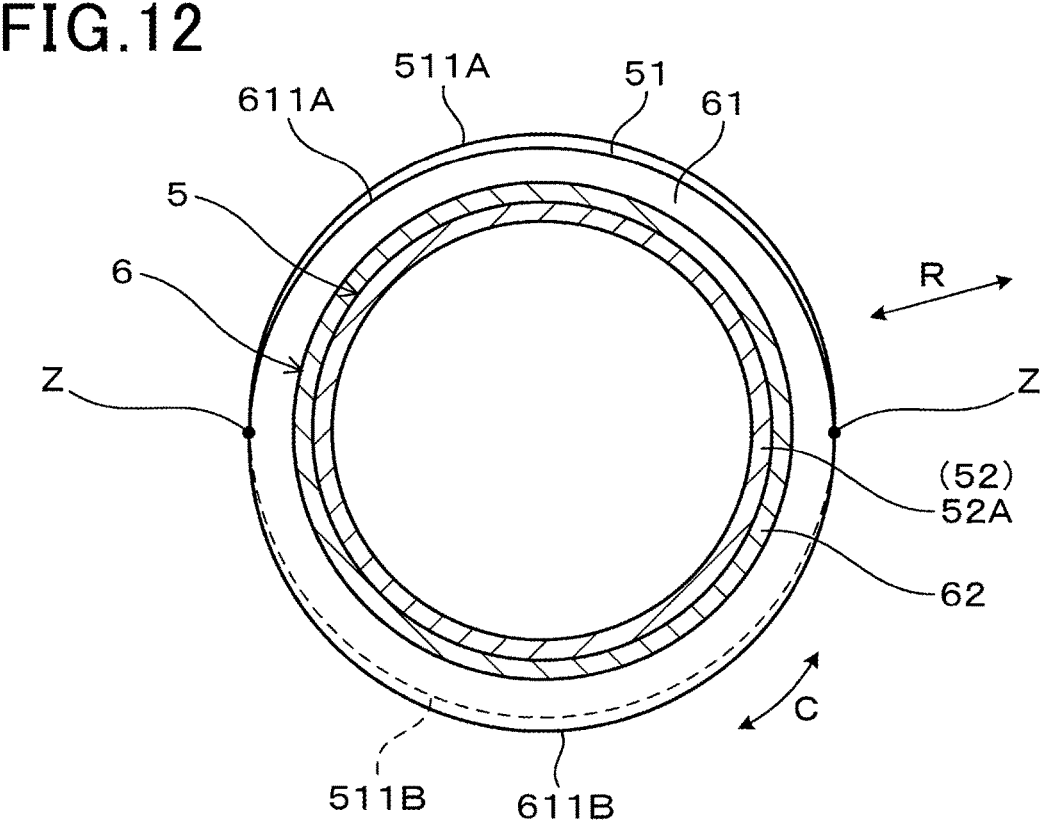
FIG. 12 is an explanatory diagram showing another inner flange portion and outer flange portion according to the first embodiment, when seen from a tip end portion of the sensor element in the insertion direction thereof.

Other than this, as shown in FIG. 12, the mutual positions between the end face 511 of the inner flange portion 51 and the end face 611 of the outer flange portion 61 can be aligned such that the center axis line of the inner cover 5 and the outer cover 6 are slightly eccentrically positioned, although the lengths of the inner flange portion 51 and the outer flange portion 61 are the same. In this case, the end face 511A of the inner flange portion 51, corresponding to half of the periphery in the circumferential direction C is positioned in the outer side R1 than the end face 611A of the outer flange portion, corresponding to half of the periphery in the circumferential direction C, and the end face 511B of the inner flange portion 51, corresponding to rest of the half periphery in the circumferential direction C is positioned in the inner side of the radial direction R than the end face 611B of the outer flange portion 61, corresponding to the remainder of the half periphery in the circumferential direction C.

Also, in the half periphery portion of the inner flange portion 51 and the outer flange portion 61, the length of the inner flange portion 51 may be longer than the length of the outer flange portion 61, whereby the end face 511A of the inner flange portion 51 may be positioned closer to the outer periphery side than the position of the end face 611A of the outer flange portion 61. In this case, in the rest of the half periphery portion of the inner flange portion 51 and the outer flange portion 61, the length of the inner flange portion 51 may be shorter than the length of the outer flange portion 61, whereby the end face 511B of the inner flange portion 51 may be positioned in the inner periphery side than the end face 611B of the outer flange portion 61.

Moreover, as shown in FIG. 10, portions Z are formed at two positions of the inner flange portion 51 and the outer flange portion 61 in the circumferential direction C, where a position of the end face 511 in the radial direction R of the inner flange portion 51 and a position of the end face 611 in the radial direction R of the outer flange portion 61 are overlapped. In this case, a gap at a boundary part between the inner flange portion 51 and the outer flange portion 61, which is likely to be formed at the overlapped portion Z, becomes minimal. Accordingly, this does not affect reduction of the load applied to the insulator opposing surface 321.

Other Gas Sensor 1

Figure 13:
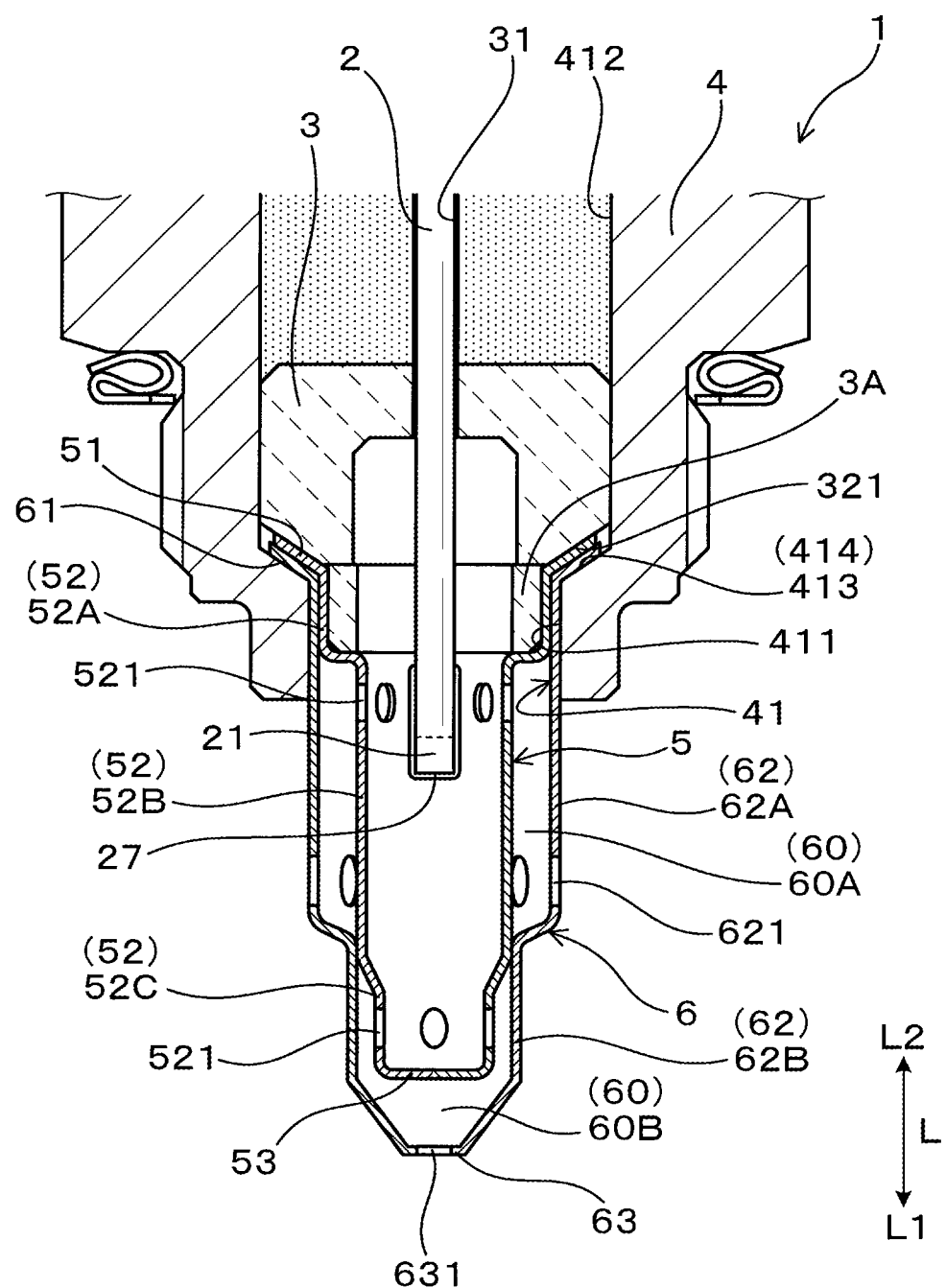
FIG. 13 is a cross-sectional view showing another gas sensor according to the first embodiment, as being enlarged in a part thereof.

As shown in FIG. 13, according to other gas sensor 1, the gas passage 60 between the inner cover 5 and the outer cover 6 may be formed to be divided into two passages such that the inner cylindrical portion 52 of the inner cover 5 and the outer cylindrical portion 62 of the outer cover 6 contact each other not only in the rear end side L2 in the insertion direction L but also in the tip end side L1 in the insertion direction.

In this case, the outer cylindrical portion 62 of the outer cover 6 is provided with a rear end outer cylindrical portion 62A positioned in the rear end side L2 of the insertion direction L, and a tip end outer cylindrical portion 62B connected to the tip end side L1 of the rear end outer cylindrical portion 62A, having smaller diameter than that of the rear end outer cylindrical portion 62A. The inner cylindrical portion 52 of the inner cover 5 includes a first inner cylindrical portion 52A, a second inner cylindrical portion, and a third inner cylindrical portion 52C. The first inner cylindrical portion 52A is attached to the outer periphery of the tip end side insulator 3A which is adjacent to the tip end side L1 of the insulator 3 in the insertion direction. The second inner cylindrical portion 52B is connected to the tip end side L1 of the first inner cylindrical portion 52A in the insertion direction L, having smaller diameter than that of the first inner cylindrical portion 52A. The third inner cylindrical portion 52C is connected to the tip end side L1 of the second inner cylindrical portion 52B in the insertion direction L, having smaller diameter than that of the second inner cylindrical portion 52B.

The rear end portion of the tip end outer cylindrical portion 62B and the tip end portion of the second inner cylindrical portion 52B are contacted with each other. Thus, the rear end side gas passage 60A is formed between the rear end outer cylindrical portion 62A and the second inner cylindrical portion 52B. The tip end side gas passage 60B is formed between the tip end outer cylindrical portion 62B and the third inner cylindrical portion 52C, and between the outer bottom portion 63 and the inner bottom portion 53.

In the other gas sensor 1, the detection gas G flowing into the rear end side gas passage 60A through the outer through hole 621 from outside the outer cover 6, flows inside the inner cover 5 through the inner through hole 521 from the rear end side gas passage 60A. The detection gas G flows into the tip end side gas passage 60B through the inner through hole 521 from inside the inner cover 5. Then, the detection gas G can flow outside the outer cover 6 through the outer through hole 631 from the tip end side gas passage 60B. According to the configuration of the inner cover 5 and the outer cover 6 in the other gas sensor 1, gas flow of the detection gas G in the gas passage 60 can be appropriately controlled.

Manufacturing Method

The inner flange portion 51 and the outer flange portion 61 are supported between the insulator 3 and the housing 4.

First, the inner cover 5 is disposed inside the outer cover 6. At this time, the inner cylindrical portion 52 and the outer cylindrical portion 62 are overlapped, and the inner flange portion 51 and the outer flange portion 61 are overlapped. Then, the inner cover 5 and the outer cover 6 are inserted in the small hole portion 411 of the support hole 41 of the housing 4. At this time, the inner flange portion 51 and the outer flange portion 61 are held by the step portion 413 of the housing 4. Note that the inner cover 5 can be disposed inside the outer cover 6 after the outer over 6 is inserted into the support hole 41.

Next, a portion in the tip end side L1 of the insulator 3 is disposed in the inner cylindrical portion 52 of the inner cover 5. Then, talc powder, the sealing member 44 such as a sleeve seal are provided in a gap formed between the housing 4 and the insulator 3 in the large hole portion 412 of the support 41 of the housing 4. After that, a portion of the housing 4 in the rear end side L2 in the insertion direction L is bent inward the radial direction R so as to caulk the housing 4 and the insulator 3 via the sealing member 44.

As shown in FIG. 7, at this time, by receiving a bending force that bends the portion of the housing 4 in the rear end side L2 inward the radial direction R, the insulator opposing surface 321 approaches the housing opposing surface 414 so that the inner flange portion 51 and the outer flange portion 61 are pressed between the insulator opposing surface 321 and the housing opposing surface 414, thereby being supported therebetween. As a result, as shown in FIG. 3, the burr 514A formed in the corner portion 513 of the inner flange portion 51 comes into contact with the insulator opposing surface 321 and is deformed, whereby the protrusion 514A is formed so as to occlude the boundary portion K1 between the insulator opposing surface 321 and the inner flange portion 51.

Effects and Advantages

According to the gas sensor 1, both of the inner flange portion 51 of the inner cover 5 and the outer flange portion 61 of the outer cover 6 are supported between the insulator opposing surface 321 and the housing opposing surface 414. That is, unlike a case where a flange portion supported between the insulator opposing surface 321 and the housing opposing surface 414, is provided at only either the inner cover 5 or the outer cover 6, the inner cover 5 and the outer cover 5 can be reliably prevented from separating from the gas sensor.

Considering a conventional gas sensor in which a flange portion is provided only for either one of the inner cover 5 or the outer cover 6, the other cover is required to be joined to either the inner cover 5 or the outer cover 6. The jointing is required to have strong enough strength to fix the other cover among the inner cover 5 and the outer cover 6 to either one cover. Hence, the volume of the joint portion becomes larger.

As a result, considering a case where the conventional gas sensor is exposed to high temperature during the operation, strength of the inner cover 5 and the outer cover 6 is remarkably decreased in the joint portion so that the inner cover 5 and the outer cover 6 may separate from the gas sensor. On the other hand, the joint portion having a large volume is not required for the gas sensor 1 in which both of the inner flange portion 51 of the inner cover 5 and the outer flange portion 61 of the outer cover 61 are supported between the insulator opposing surface 321 and the housing opposing surface 414. Hence, the inner cover 5 or the outer cover 6 can be prevented from separating from the gas sensor during the operation thereof.

It is preferable that the joint portion is not formed using a welding or the like between the inner cylindrical portion 52 of the inner cover 5 and the outer cylindrical portion 62 of the outer cover 62. However, a joint portion having smaller volume may be formed, by welding or the like, between the inner cylindrical portion 52 of the inner cover 5 and the outer cylindrical portion 62 of the outer cover 6, in order to keep the positional relationship therebetween. An allowable volume of the joint portion to be formed can be determined within a range such that degree of a decrease in the strength during the heating does not cause separating of the inner cover 5 and the outer cover 6.

According to the gas sensor 1 of the present embodiment, although the protrusion 514 that contacts the insulator opposing surface 321 is formed in the corner portion 513 that faces the insulator opposing surface 321, the end face 611 of the outer flange portion 61 is offset towards the outer side R1 in the radial direction R more than the end face 511 of the inner flange portion 51. Thus, in the inner flange portion 51, the load applied to the insulator opposing surface 321 from the protrusion 514 of the corner portion 513 that faces the insulator opposing surface 321 can be reduced.

Figure 14:
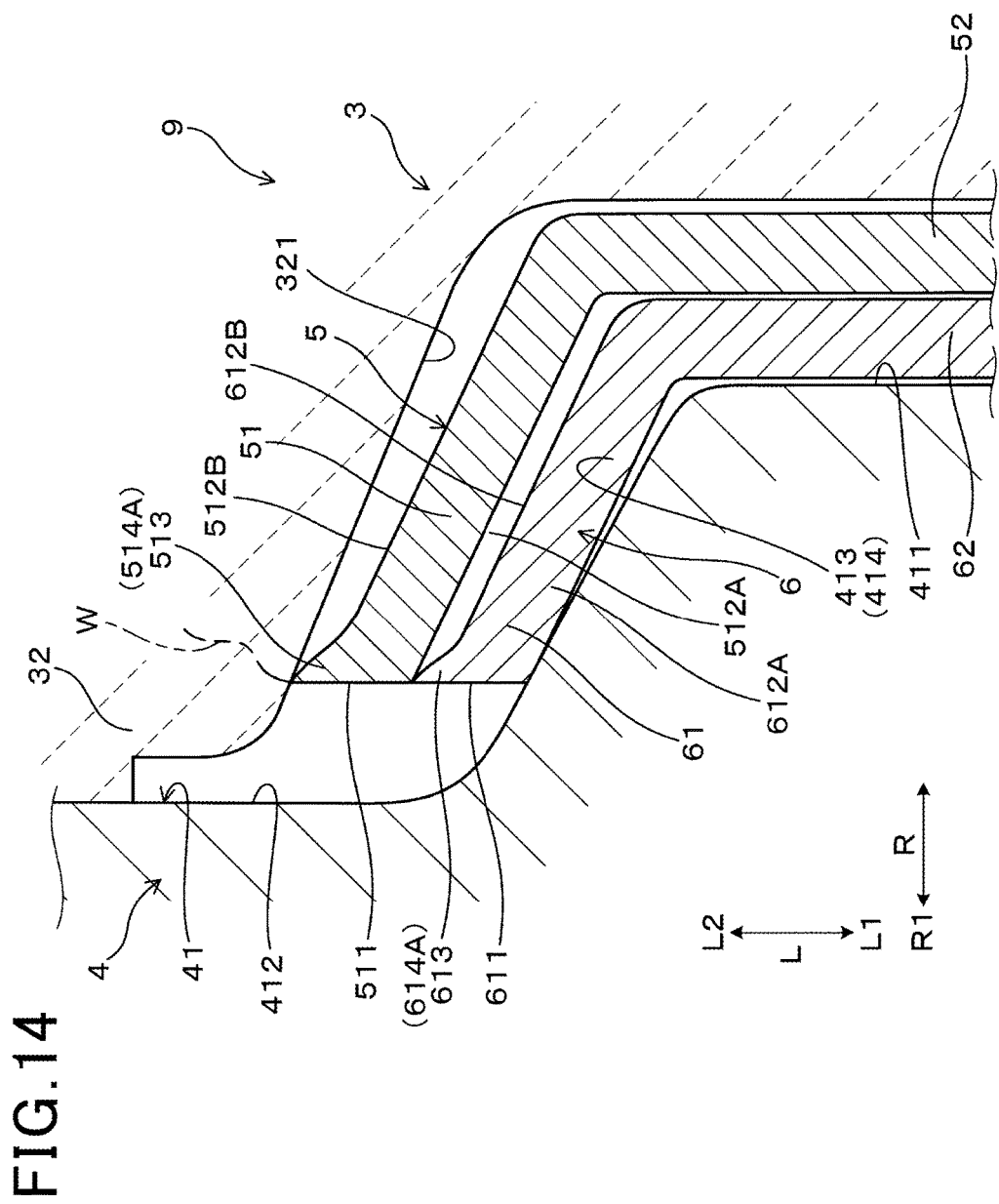
FIG. 14 is a cross-sectional view showing an enlargement of a peripheral portion of an inner flange portion and an outer flange portion supported between the insulator and the housing according to a comparative embodiment.

More specifically, similar to the case of the corner portion 513 in the inner flange portion 51, in the outer flange portion 61, the burr 614A is formed in the corner portion 613 that faces the inner flange portion 51. In this case, as shown in FIG. 14, in the conventional gas sensor 9, when the end face 511 of the inner flange portion 51 and the end face 611 of the outer flange portion 61 are flush with each other, the burr 514A in the inner flange portion 51 and the burr 614A in the outer flange portion 61 are overlapped in the insertion direction L.

Then, when the inner flange portion 51 and the outer flange portion 61 are disposed between the insulator opposing surface 321 and the housing opposing surface 414, it is required to increase a calking force generated when a portion of the housing 4 in the rear end side L2 is deformed inwardly with respect to the radial direction R in order to secure the air tightness between the insulator opposing surface 321 and the housing opposing surface 414. At this moment, the burr 514A in the inner flange portion 51 and the burr 614A in the outer flange portion 61 are overlapped, thereby increasing a load applied to the insulator opposing surface 321 from the burr 514A in the inner flange portion 51. When the load applied to the insulator opposing surface 321 exceeds the strength of the ceramic material that composes the insulator 3, a crack W may occur on the insulator opposing surface 321.

On the other hand, according to the gas sensor 1 of the present embodiment, since the end face 611 of the outer flange portion 61 is offset towards the outer side R1 in the radial direction than the end face 511 of the inner flange portion 51, whereby the burr 614A in the outer flange portion 61 is positioned in the outer side R1 in the radial direction than the burr 514A in the inner flange portion 51. Thus, almost no load is applied to the burr 614A of the outer flange portion 61 so that a load applied to the insulator opposing surface 321 from the burr 514A in the inner flange portion 51 can be reduced. Therefore, occurrence of cracks W on the insulator opposing surface 321 can be avoided.

As a result, according to the gas sensor 1 of the present embodiment, the possibility of separating of the outer cover 5 or the inner cover 6 during the operation of the gas sensor 1 can be avoided, and also breakage of the insulator 3 can be avoided.

Second Embodiment

The present embodiment will be described only for a case where an alignment of the positional offset between the end face 511 of the inner flange portion 51 and the end face 611 of the outer flange portion 61 is different from that of the first embodiment.

Figure 15:
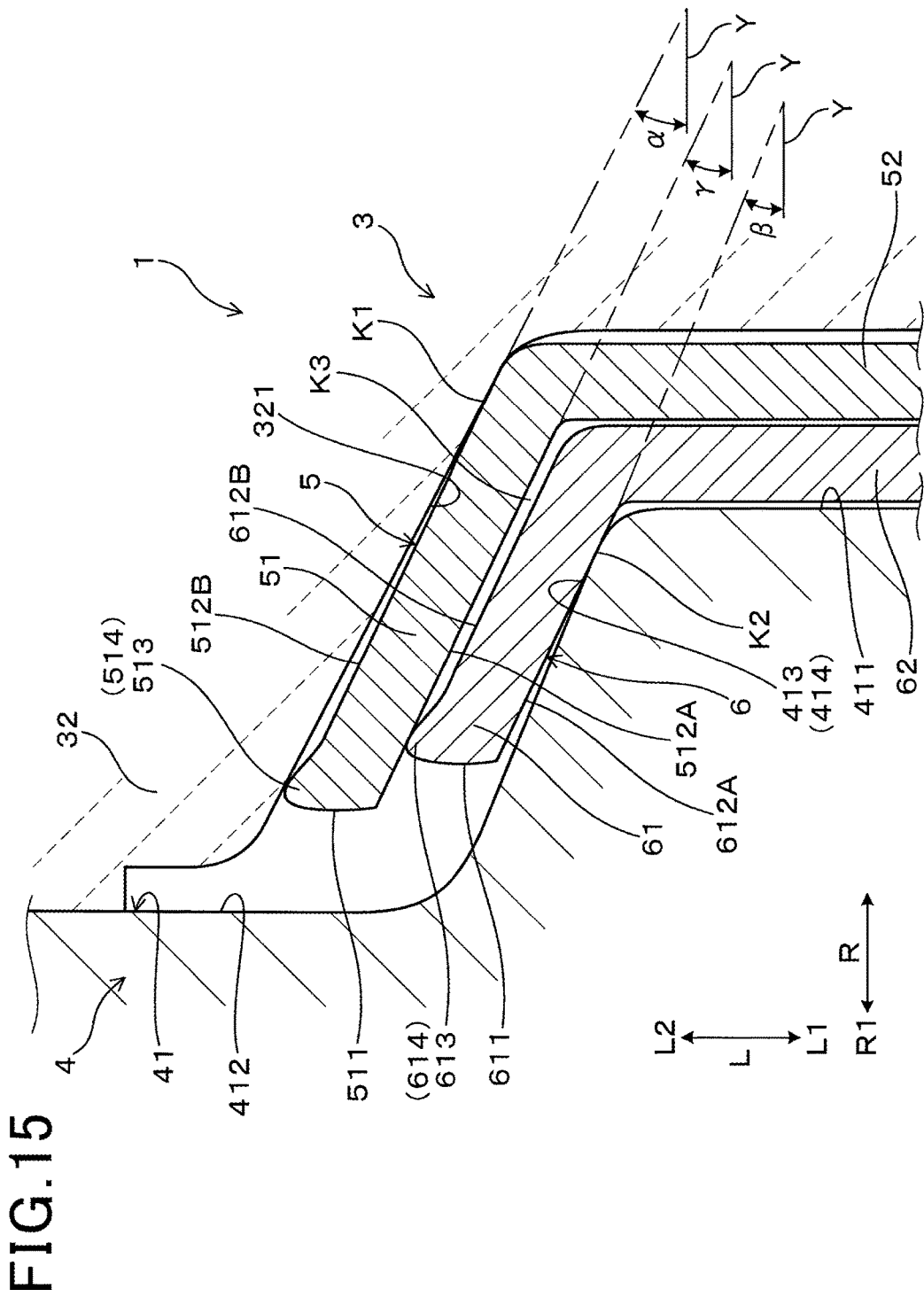
FIG. 15 is a cross-sectional view showing an enlargement of a peripheral portion of an inner flange portion and an outer flange portion supported between the insulator and the housing according to a second embodiment.

According to the gas sensor 1 of the present embodiment, as shown in FIG. 15, the end face 511 of the entire periphery of the inner flange portion 51 in the circumferential direction C is positioned radially closer to the outer side R1 with respect to the radial direction R than the position of the end face 611 of the entire periphery of the outer flange portion 61 in the circumferential direction C. In the inner flange portion 51, the protrusion 514, in which the burr 514A is plastically deformed, is formed in the corner portion 513 between the end 511 and the surface 512B in the rear end side L2. Further, in the outer flange portion 61, the protrusion 614, in which the burr 614A is plastically deformed, is formed in the corner portion 613 between the end face 611 and the surface 612B in the rear end side L2 in the insertion direction L. The protrusion 514 contacts the insulator opposing surface 321, and the protrusion 614 contacts the inner flange portion 51.

Figure 16:
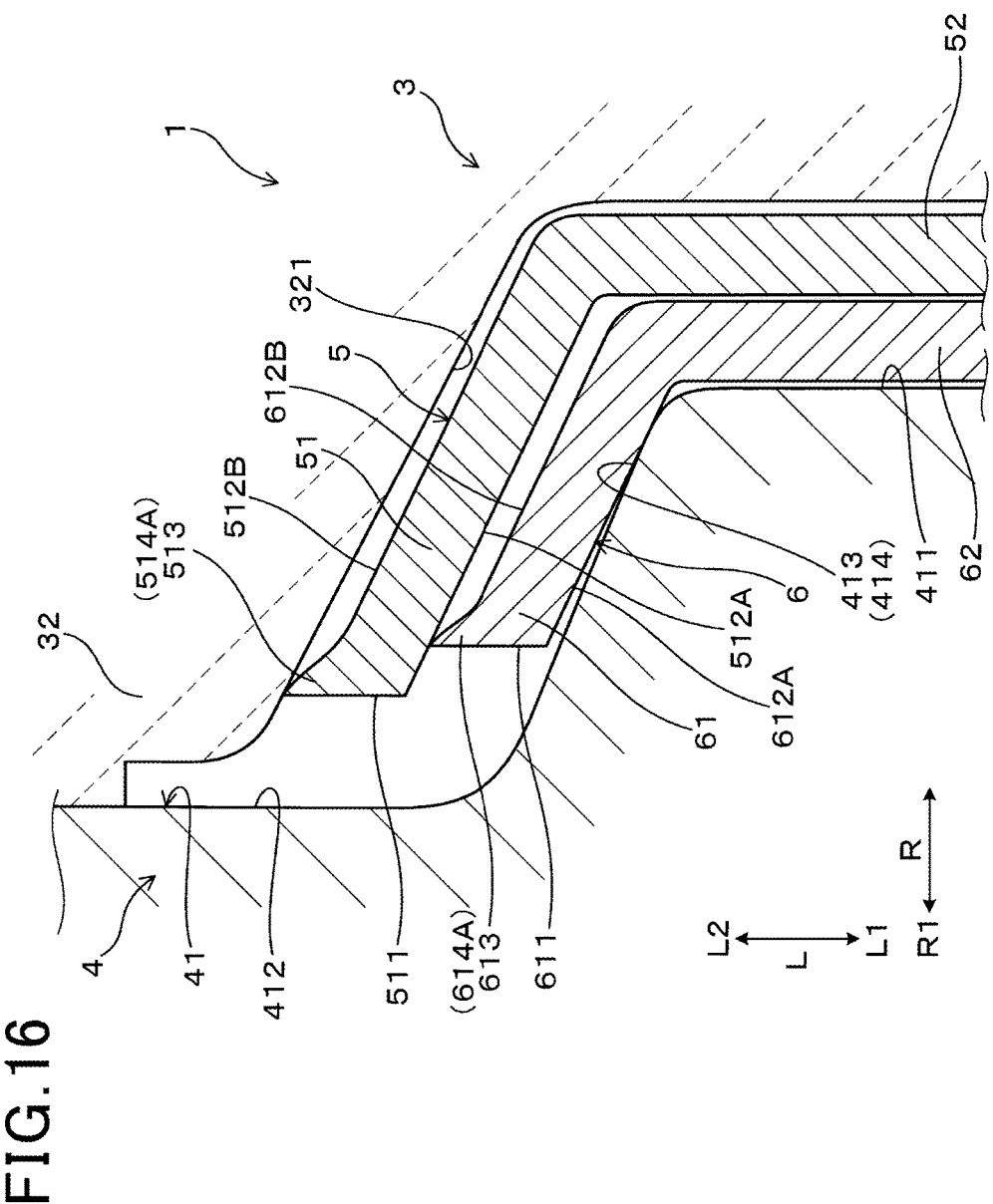
FIG. 16 is a cross-sectional view showing an enlargement of a peripheral portion of an inner flange portion and an outer flange portion before being supported between the insulator and the housing according to the second embodiment.

As shown in FIG. 16, in an initial state of the inner cover 5 and the outer cover 6 before assembling the gas sensor 1, the end face 511 of the inner flange portion 51 is formed approximately parallel to the insertion direction L, and also the end face 611 of the outer flange portion 61 is formed approximately parallel to the insertion direction L. Also, in this initial state, the burr 514A is formed in the corner portion 513 in the inner flange portion 51, in which part of the material is protruded.

As shown in FIG. 15, when the inner flange portion 51 and the outer flange portion 61 are disposed between the insulator opposing surface 321 and the housing opposing surface 414, the burr 514A in the inner flange portion 51 contacts with the insulator opposing surface 321 and is deformed. The burr 614A in the outer flange portion 61 contacts with the surface 512A in the tip end side L1 of the inner flange portion 51 and is deformed. The boundary portion K1 between the insulator opposing 321 and the surface 512B of the inner flange portion 51 is closed by the protrusion 514 in which the burr 514A is plastically deformed. Moreover, the boundary portion K3 between the surface 512A of the inner flange portion 51 and the surface 612B of the outer flange portion 61 is closed by the protrusion 614 in which the burr 514A is plastically deformed. The boundary portion K2 between the housing opposing surface 414 and the surface 612A of the outer flange portion 61 is closed by these surfaces which are closely contacted. The end face 511 of the inner flange portion 51 and the end face 611 of the outer flange portion 61 after assembling the gas sensor 1 may be inclined with respect to the insertion direction L or may be bent to have a curved surface.

According to the gas sensor 1 of the present embodiment, a gap is unlikely to be formed between the surface 512A of the inner flange portion 51 and the surface 612B of the outer flange portion 61. According to the present embodiment, not only the burr 514A in the inner flange portion 51 is deformed but also the burr 614A in the outer flange portion 61 is deformed, whereby the load applied to the insulator opposing surface 321 becomes larger compared to the first embodiment. However, the protrusion 514 of the inner flange portion 51 and the protrusion 614 of the outer flange portion 61 are offset in the radial direction R, whereby a crack W is unlikely to occur on the insulator opposing surface 321.

According to the present embodiment, a relationship between the inclination angle α of the insulator opposing surface 321, the inclination angle β of the housing opposing surface 414 and the inclination angle γ of the inner flange portion 51 and the outer flange portion 61 are similar to that of the first embodiment. Moreover, other configurations of the gas sensor 1, effects and advantages or the like are the same as that of the first embodiment. According to the present embodiment, elements having the same reference signs as the first embodiment are the same as the element of the first embodiment.

Confirmation Test

According to the present confirmation test, a test for confirming whether cracking occurs in the insulator 3, and a test for whether gas leakage occurs in a gap between the insulator 3 and the housing 4 were performed for the gas sensor 1 (test sample) described in the first and second embodiments. For the comparison, as a comparative sample, the gas sensor 9 (see FIG. 12) is used in which a position of the end face 511 of the inner flange portion 51 in the radial direction R and a position of the end face 611 of the outer flange portion 61 are flushed with each other. Then, each test was performed for the comparative samples as well.

In the crack confirmation test, assembled gas sensors 1, 9 were disassembled to draw out the insulators 3. Thereafter, the insulator 3 drawn out from the gas sensors was immersed in a stain solution, and it was confirmed whether any cracks were present in the insulators by using properties that the stain solution permeates cracks. Specifically, 10 samples of insulators 3 drawn out from the gas sensors were examined to confirm whether cracks were present. In the evaluation of whether cracks were present, when one or more cracks out of 10 samples was observed, it was expressed as "fail" in table 1 which will be described later, and when no cracks were observed in the 10 samples, it was expressed as "pass" in table 1.

In the leakage confirmation test, pressure of the exhaust gas in the pipe was set to be higher than the atmospheric pressure of the reference gas A, in which a pressure difference therebetween was set to be 40 kPa. The inner flange portion 51 and the outer flange portion 61 were heated such that the temperature thereof became 600° C. Then, a cold-heat cycle was performed for more than 100 times so as to cool the inner flange portion 51 and the outer flange portion 61 such that the temperature thereof became 25° C. as the room temperature, thereby heating and cooling the gas sensors 1, 9 of the test sample and the comparative sample. While repeating the cold-heat cycle, a mass flow meter measured an amount of flow of the exhaust gas that flows a gap between the insulator 3 and the housing 4, and the total accumulated amount of the gas flow was calculated as an amount of leakage.

In the leakage confirmation test, the required output accuracy of the gas sensors 1, 9 is determined for the gas detection, and an amount of leakage limit required for securing the output accuracy is determined. In the confirmation test, when an amount of leakage measured for the gas sensors 1 and 9 exceeds the leakage limit, it is expressed as "fail" in table 1, and when the amount of leakage is less than or equal to the leakage limit, it is expressed as "pass" in table 1.

The crack confirmation test and the leakage confirmation test were performed under various conditions of the insulator opposing surface 321, the housing opposing surface 414, the inner flange portion 51 and the outer flange portion 61.

The conditions include relationships between an inclination angle $\alpha$ of the insulator opposing surface 321, an inclination angle $\beta$ of the housing opposing surface 414, and the inclination angle $\gamma$ of the inner flange portion 51 and the outer flange portion 61, such as $\beta \leq \gamma < \alpha$, and $\alpha = \beta = \gamma$. Further, the conditions include a case where the end face 511 of the entire periphery of the inner flange portion 51 in the circumferential direction C is positioned radially closer to the outer side R1 with respect to the radial direction R than the position of the end face 611 of the entire periphery of the outer flange portion 61 in the circumferential direction C (expressed as $\Delta L=+$, refer to FIG. 15), and a case where the end face 611 of the entire periphery of the outer flange portion 61 in the circumferential direction C is positioned radially closer to the outer side R1 with respect to the radial direction R than the position of the end face 511 of the entire periphery of the inner flange portion 51 in the circumferential direction C (expressed as $\Delta L=-$, refer to FIG. 3). Note that $\Delta L$ refers to a distance between the end face 511 of the inner flange portion 51 and the end face 611 of the outer flange portion 61.

Further, the condition includes a case where the end face 511 of a half periphery of the inner flange portion 51 in the circumferential direction C is positioned radially closer to the outer side R1 with respect to the radial direction R than the position of the end face 611 of the half periphery of outer flange portion 61 in the circumferential direction C, and the end face 511 of the remaining periphery is positioned radially closer to an inner side with respect to the radial direction R than the position of the end face 611 of the remaining half periphery ($\Delta L=\pm$, refer to FIG. 12); and a case where the position of the end face 611 of the entire periphery of the outer flange portion 61 in the circumferential direction C and the position of the end face 511 of the entire periphery of the inner flange portion 51 in the circumferential direction C are the same ($\Delta L=0$).

Table 1 shows conditions of the confirmation test for the test samples 1 to 6 and the comparative samples 1 and 2, in which a condition of the inclination angle is $\beta \leq \gamma < \alpha$ or $\alpha = \beta = \gamma$, and a positional relationship between the end face 511 of the inner flange portion 51 and the end face 611 of the outer flange portion 61 is $\Delta L=+$, $\Delta L=-$, $\Delta L=\pm$ or $\Delta L=0$. Also, table 1 includes evaluation results of the crack confirmation test and the leakage confirmation test for the test samples 1 to 6 and the comparative samples.

TABLE 1

| | Conditions | Crack confirmation test result | Leakage confirmation test result |
|---|---|---|---|
| test sample 1 | $\beta \leq \gamma < \alpha$, $\Delta L = +$ | pass | pass |
| test sample 2 | $\beta \leq \gamma < \alpha$, $\Delta L = -$ | Pass | Pass |
| test sample 3 | $\alpha = \beta = \gamma$, $\Delta L = +$ | Pass | Pass |
| test sample 4 | $\alpha = \beta = \gamma$, $\Delta L = -$ | Pass | Pass |
| test sample 5 | $\beta \leq \gamma < \alpha$, $\Delta L = \pm$ | Pass | Pass |
| test sample 6 | $\alpha = \beta = \gamma$, $\Delta L = \pm$ | Pass | Pass |
| comparative sample 1 | $\beta \leq \gamma < \alpha$, $\Delta L = 0$ | Fail | Fail |
| comparative sample 2 | $\alpha = \beta = \gamma$, $\Delta L = 0$ | Fail | Fail |

As illustrated in the table 1, the crack confirmation test results of the test samples 1 and 2 with the condition of $\beta \leq \gamma < \alpha$ and either $\Delta L=+$ or $-$ were pass, since no cracks were observed on the insulator 3, and the leakage confirmation test results of the test samples 1 and 2 were pass, since an amount of leakage is smaller than or equal to the leakage limit. Likewise, the crack confirmation test results of the test samples 3 and 4 with the condition of $\alpha = \beta = \gamma$ and either $\Delta L=+$ or $-$ were pass, since no cracks were observed on the insulator 3, and the leakage confirmation test results of the test samples 3 and 4 were pass, since an amount of leakage is smaller than or equal to the leakage limit.

Similarly, the crack confirmation test results of the test samples 5 and 6 with the condition of $\beta \leq \gamma < \alpha$ and either $\Delta L=+$ or $-$ were pass since no cracks were observed on the insulator 3, and the leakage confirmation test results of the test samples 5 and 6 were pass since an amount of leakage is smaller than or equal to the leakage limit. On the other hand, for the comparative samples 1 and 2 having relationships $\beta \leq \gamma < \alpha$ and $\Delta L=0$, the crack confirmation test results were fail since cracks were observed on the insulator 3, and the leakage confirmation test results were fail since the leakage exceeded the leakage limit.

According to results of the crack confirmation test and the leakage confirmation test, it has been found that cracks are unlikely to occur in the insulator 3 and gas leakage is unlikely to occur between the insulator 3 and the housing 4, since the position of the end face 511 of the inner flange portion 51 and the position of the end face 611 of the outer flange portion 61 are offset. Further, in addition to the positional offset between the end face 511 and the end face 611, a relationship of $\beta \leq \gamma < \alpha$ is satisfied so that gas leakage between the insulator 3 and the housing 4 is suppressed and also cracks are unlikely to occur on the insulator 3.

The present disclosure is not limited to the above-described embodiments. Moreover, the embodiments can be modified in various ways without departing the scope of the present disclosure.

What is claimed is:

1. A gas sensor comprising:
a sensor element having a detecting portion exposed to detection gas to perform gas detection;
an insulator made of ceramic material, supporting the sensor element in a state where the detecting portion is protruded therefrom, the sensor element being inserted through the insulator;
a housing made of metal disposed in an outer periphery of the insulator, supporting the insulator;
an inner cover made of metal, covering the detecting portion and having an inner through hole that allows the detection gas to flow therethrough; and
an outer cover made of metal, covering the inner cover such that a gas passage through which the detection gas flows is formed between the outer cover and the inner cover and having an outer through hole that allows the detection gas to flow therethrough,
wherein
an inner flange portion formed over an entire periphery of an end portion of the inner cover and an outer flange portion formed over an entire periphery of an end portion of the outer cover are supported between the insulator and the housing;
a protrusion is formed on a corner portion of the inner flange portion, the corner portion facing the insulator and the protrusion contacting with the insulator; and
an end face of the inner flange portion and an end face of the outer flange portion are mutually offset.

2. The gas sensor according to claim 1, wherein
the end face of the outer flange portion is positioned radially closer to an outer side with respect to a radial direction, than a position of the end face of the inner flange portion, where an insertion direction is defined as a direction along which the sensor element is inserted into the insulator, and the radial direction is defined as a direction orthogonal to the insertion direction, extending from a center axis line that passes through a center of the sensor element along the insertion direction.

3. The gas sensor according to claim 2, wherein
a protrusion is formed on a corner portion of the outer flange portion, the corner portion facing the inner flange portion and the protrusion not contacting with the inner flange portion.

4. The gas sensor according to claim 1, wherein
the end face of the inner flange portion is positioned radially closer to an outer side with respect to a radial direction, than a position of the end face of the outer flange portion, where an insertion direction is defined as a direction along which the sensor element is inserted into the insulator, and the radial direction is defined as a direction orthogonal to the insertion direction, extending from a center axis line that passes a center of the sensor element along the insertion direction.

5. The gas sensor according to claim 4, wherein
a protrusion is formed on a corner portion of the outer flange portion, the corner portion facing the inner flange portion and the protrusion not contacting with the inner flange portion.

6. The gas sensor according to claim 2, wherein
a tip end side is defined as a side in the insertion direction, where the detecting portion is protruded from the sensor element, and a rear end portion is defined as a side opposite to the tip end side;
the inner flange portion and the outer flange portion are each formed to be inclined such that positions of the inner flange portion and the outer flange portion with respect to the insertion direction become closer to the rear end side, as positions of the inner flange portion and the outer flange portion with respect to the radial direction become closer to the outer side;
an insulator opposing surface that faces the inner flange portion is formed on an entire outer periphery of the insulator;
a housing opposing surface that faces the outer flange portion is formed on an entire inner periphery, and
a relationship of $\beta \leq \gamma < \alpha$ or $\beta < \gamma \leq \alpha$ is satisfied, where an inclination angle of the insulation opposing surface with respect to a virtual reference line parallel to the radial direction is defined as $\alpha$, an inclination angle of the housing opposing surface with respect to the virtual reference line is $\beta$ and an inclination angle of the inner flange portion and the outer flange portion with respect to the virtual reference line is $\gamma$.

* * * * *